(12) United States Patent
Kuramoto

(10) Patent No.: US 12,279,756 B2
(45) Date of Patent: Apr. 22, 2025

(54) ENDOSCOPE SYSTEM FOR OBSERVING CHEMICAL FLUORESCENCE AND METHOD OF OPERATING THE SAME

(71) Applicant: FUJIFILM Corporation, Tokyo (JP)

(72) Inventor: Masayuki Kuramoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 543 days.

(21) Appl. No.: 17/702,226

(22) Filed: Mar. 23, 2022

(65) Prior Publication Data

US 2022/0211259 A1 Jul. 7, 2022

Related U.S. Application Data

(63) Continuation of application No. PCT/JP2020/035328, filed on Sep. 17, 2020.

(30) Foreign Application Priority Data

Sep. 24, 2019 (JP) .................................. 2019-172952

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/00006* (2013.01); *A61B 1/000094* (2022.02);
(Continued)

(58) Field of Classification Search
None
See application file for complete search history.

(56) References Cited

U.S. PATENT DOCUMENTS 5,092,331 A 3/1992 Nakamura et al.
2002/0175993 A1* 11/2002 Ueno .................... A61B 5/0071
348/68

(Continued)

FOREIGN PATENT DOCUMENTS

JP H02-299633 A 12/1990
JP 2003-126014 A 5/2003
(Continued)

OTHER PUBLICATIONS

International Search Report issued in PCT/JP2020/035328; mailed Oct. 20, 2020.
(Continued)

*Primary Examiner* — John P Leubecker
(74) *Attorney, Agent, or Firm* — Studebaker Brackett PLLC

(57) ABSTRACT

A light source unit emits excitation light, which causes a drug to be excited to emit chemical fluorescence, and reference light which has a wavelength range from a blue-light wavelength range to a red-light wavelength range. A color information acquisition section acquires a plurality of pieces of color information from fluorescence and reference image signals that are obtained from the image pickup of an object to be observed illuminated with the excitation light and the reference light. A color difference expansion section expands a color difference between a normal mucous membrane and a fluorescence region in a feature space formed by the plurality of pieces of color information.

13 Claims, 31 Drawing Sheets

(51) Int. Cl.
*A61B 1/06* (2006.01)
*G06T 7/00* (2017.01)
*G06T 7/90* (2017.01)

(52) U.S. Cl.
CPC ...... *A61B 1/000095* (2022.02); *A61B 1/0638* (2013.01); *A61B 1/0653* (2013.01); *G06T 7/0014* (2013.01); *G06T 7/90* (2017.01); *G06T 2207/10064* (2013.01); *G06T 2207/10068* (2013.01); *G06T 2207/30096* (2013.01)

(56) References Cited

U.S. PATENT DOCUMENTS

| | | | |
|---|---|---|---|
| 2004/0037454 A1* | 2/2004 | Ozawa | A61B 1/000094 382/128 |
| 2005/0206979 A1* | 9/2005 | Tomizawa | G09G 5/026 358/1.9 |
| 2011/0164127 A1 | 7/2011 | Stehle et al. | |
| 2015/0269741 A1* | 9/2015 | Moriya | H04N 1/622 382/164 |
| 2015/0269750 A1* | 9/2015 | Moriya | H04N 1/622 382/128 |
| 2015/0374263 A1* | 12/2015 | Kuramoto | A61B 5/1032 600/477 |
| 2015/0379698 A1* | 12/2015 | Kuramoto | H04N 1/6027 382/128 |
| 2016/0007829 A1* | 1/2016 | Chun | G06T 5/92 600/103 |
| 2016/0007830 A1* | 1/2016 | Chun | A61B 1/000094 600/476 |
| 2016/0029925 A1* | 2/2016 | Kuramoto | A61B 1/0653 348/65 |
| 2016/0093067 A1* | 3/2016 | Kuramoto | G06V 10/60 382/128 |
| 2016/0171718 A1* | 6/2016 | Kuramoto | A61B 5/0084 382/128 |
| 2016/0239965 A1* | 8/2016 | Kuramoto | G06T 7/0012 |
| 2017/0018083 A1* | 1/2017 | Kuramoto | A61B 5/073 |
| 2017/0032539 A1* | 2/2017 | Kuramoto | A61B 1/0005 |
| 2019/0021580 A1* | 1/2019 | Mishima | A61B 1/0638 |

FOREIGN PATENT DOCUMENTS

| | | |
|---|---|---|
| JP | 2004-024611 A | 1/2004 |
| JP | 2006-122234 A | 5/2006 |
| JP | 2011-522649 A | 8/2011 |
| JP | 2017-023620 A | 2/2017 |
| JP | 2018-175762 A | 11/2018 |

OTHER PUBLICATIONS

International Preliminary Report on Patentability and Written Opinion issued in PCT/JP2020/035328; issued Mar. 15, 2022.
An Office Action; "Notice of Reasons for Refusal," mailed by the Japanese Patent Office on Oct. 25, 2022, which corresponds to Japanese Patent Application No. 2021-548867 and is related to U.S. Appl. No. 17/702,226; with English language translation.

* cited by examiner

FIG. 18
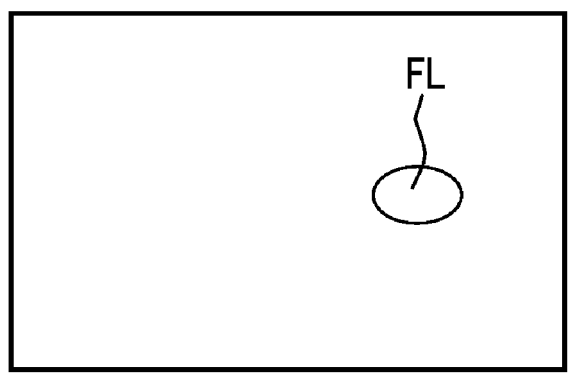
R-IMAGE SIGNAL
OF FLUORESCENCE IMAGE SIGNAL
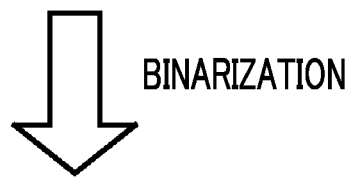
BINARIZATION
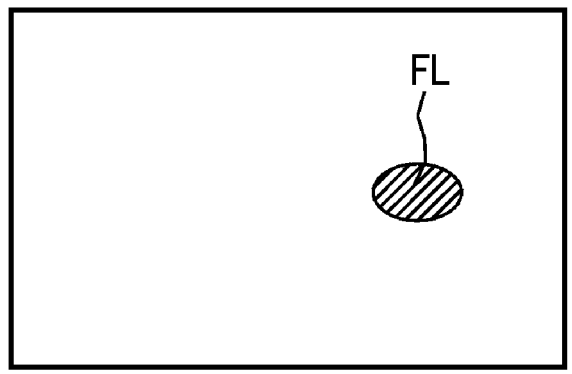
BINARIZED FLUORESCENCE IMAGE

FIG. 24

|  | BEFORE CORRECTION | AFTER CORRECTION |
|---|---|---|
| PIXEL VALUE OF FLUORESCENCE | 15 | 80 |
| PIXEL VALUE OF FLUORESCENCE AND REFERENCE LIGHT | 165 | 230 |
| PIXEL VALUES OF REFERENCE LIGHT | 150 | 150 |
| R-GAIN COEFFICIENT FOR FLUORESCENCE OBSERVATION | 1.5 | 8 |
| AMOUNT OF FLUORESCENCE | 10 | 10 |
| AMOUNT OF REFERENCE LIGHT | 100 | 18.75 |

ENDOSCOPE SYSTEM FOR OBSERVING CHEMICAL FLUORESCENCE AND METHOD OF OPERATING THE SAME

CROSS-REFERENCE TO RELATED APPLICATIONS

This application is a Continuation of PCT International Application No. PCT/JP2020/035328 filed on 17 Sep. 2020, which claims priority under 35 U.S.C § 119(a) to Japanese Patent Application No. 2019-172952 filed on 24 Sep. 2019. The above application is hereby expressly incorporated by reference, in its entirety, into the present application.

BACKGROUND OF THE INVENTION

1. Field of the Invention

The present invention relates to an endoscope system that is used to observe chemical fluorescence emitted from a drug given to a patient, and a method of operating the endoscope system.

2. Description of the Related Art

An endoscope system comprising a light source device, an endoscope, and a processor device has been widely used in a medical field in recent years. In the endoscope system, an object to be observed is irradiated with illumination light from the endoscope, and the image of the object to be observed is displayed on a monitor on the basis of RGB image signals that are obtained in a case where the image of the object to be observed, which is being illuminated with the illumination light, is picked up by an image pickup element of the endoscope.

Further, as disclosed in Photodynamic diagnosis (PDD), etc., [online], [Search on Jul. 2, 2019], Internet <URL: https://home.hiroshima-u.ac.jp/urology/whatsnew-PD-D.html>, in a diagnosis using an endoscope, in a state where a drug having an affinity for a lesion area is given to a patient and is selectively accumulated, an object to be observed of the patient is irradiated with excitation light so that chemical fluorescence is excited and emitted from the drug contained in the object to be observed. However, in a case where the object to be observed is irradiated with only blue excitation light, the object to be observed is displayed on a monitor as a bluish image that is difficult to be visually recognized by a user (see Photodynamic diagnosis (PDD), etc., [online], [Search on Jul. 2, 2019], Internet <URL:https://home.hiroshima-u.ac.jp/urology/whatsnew-PDD.html>). Accordingly, a user needs to be accustomed to the bluish image to some extent for a screening purpose for detecting a lesion area. Therefore, in JP2006-122234A, a normal image is combined with a fluorescence image and a composite image is displayed on a monitor. As a result, even in a case where a user is not accustomed to fluorescence observation, an image is displayed with a color to be likely to be visually recognized by a user so that the user easily performs fluorescence observation. However, there is a problem that a frame rate drops since the images are always combined and displayed.

SUMMARY OF THE INVENTION

It may be difficult to see a difference between a fluorescence region, which includes chemical fluorescence, and a region in which the drug is not accumulated, such as a normal mucous membrane, in a fluorescence image. For example, in a case where the object to be observed is irradiated with blue excitation light to emit red chemical fluorescence and the normal mucous membrane is reddish as a whole, it is difficult to see a difference in color between the normal mucous membrane and the fluorescence region.

An object of the present invention is to provide an endoscope system that can display an image with a color to be likely to be visually recognized by a user and improve the visibility of a fluorescence region by making a difference in color between a normal mucous membrane and the fluorescence region, and a method of operating the endoscope system.

An endoscope system according to an aspect of the present invention comprises: a light source unit that emits excitation light, which causes a drug contained in an object to be observed to be excited to emit chemical fluorescence, and reference light which has at least a wavelength range from a blue-light wavelength range to a red-light wavelength range; and an image control processor. Fluorescence and reference image signals, which are obtained from image pickup of the object to be observed illuminated with the excitation light and the reference light, are input to the image control processor; and the image control processor acquires a plurality of pieces of color information from the fluorescence and reference image signals and expands a color difference between a normal mucous membrane and a fluorescence region, which includes the chemical fluorescence, in a feature space formed by the plurality of pieces of color information.

It is preferable that the color difference between the normal mucous membrane and the fluorescence region is increased by being expanded around an expansion center determined in the feature space. It is preferable that the image control processor changes the expansion center on the basis of the fluorescence and reference image signals and fluorescence image signals obtained from image pickup of the object to be observed illuminated with only the excitation light. It is preferable that the image control processor changes the expansion center on the basis of reference image signals obtained from a difference between the fluorescence and reference image signals and the fluorescence image signals. It is preferable that the image control processor calculates an amount of change of the expansion center on the basis of components of fluorescence and reference light included in the fluorescence and reference image signals and components of fluorescence included in the fluorescence image signals.

It is preferable that the image control processor generates a first lesion image in which a lesion area including components of the fluorescence and reference light is displayed and a lesion-excluding image in which portions other than the lesion area including the components of the fluorescence and the reference light are displayed, from the fluorescence and reference image signals and the fluorescence image signals, and calculates an amount of change of the expansion center on the basis of the first lesion image and the lesion-excluding image.

It is preferable that the endoscope system further comprises a light source processor switching a reference frame where the excitation light and the reference light are emitted and a fluorescence frame where only the excitation light is emitted at a specific number of frames. It is preferable that the image control processor calculates an amount of the fluorescence and an amount of the reference light on the basis of the fluorescence and reference image signals and fluorescence image signals obtained at the fluorescence frame.

It is preferable that the image control processor acquires a first lesion image in which a lesion area including components of the fluorescence and reference light is displayed and a second lesion image in which a lesion area including components of the fluorescence is displayed, on the basis of the fluorescence and reference image signals and the fluorescence image signals, and calculates an amount of the fluorescence and an amount of the reference light on the basis of the first lesion image and the second lesion image.

It is preferable that the image control processor changes contents of processing to be performed on the fluorescence and reference image signals on the basis of the amount of the fluorescence and the amount of the reference light. It is preferable that the contents of the processing are gain processing or matrix processing. It is preferable that the image control processor corrects the amount of the reference light on the basis of the contents of the processing before and after the change.

A method of operating an endoscope system according to another aspect of the present invention comprises: a step of emitting excitation light, which causes a drug contained in an object to be observed to be excited to emit chemical fluorescence, and reference light which has a wavelength range from a blue-light wavelength range to a red-light wavelength range; a step of inputting fluorescence and reference image signals that are obtained from image pickup of the object to be observed illuminated with the excitation light and the reference light; a step of acquiring a plurality of pieces of color information from the fluorescence and reference image signals; and a step of expanding a color difference between a normal mucous membrane and a fluorescence region, which includes the chemical fluorescence, in a feature space formed by the plurality of pieces of color information.

According to the present invention, it is possible to display an image with a color to be likely to be visually recognized by a user and to improve the visibility of a fluorescence region by making a difference in color between a normal mucous membrane and the fluorescence region.

BRIEF DESCRIPTION OF THE DRAWINGS

FIG. 18 is a diagram illustrating a method of generating a binarized fluorescence image.

FIG. 24 is a table showing the pixel values of fluorescence, the pixel values of fluorescence and reference light, the pixel values of reference light, R-gain coefficients for fluorescence observation, the amounts of fluorescence, and the amounts of reference light before and after correction.

DESCRIPTION OF THE PREFERRED EMBODIMENTS

First Embodiment

Figure 1:
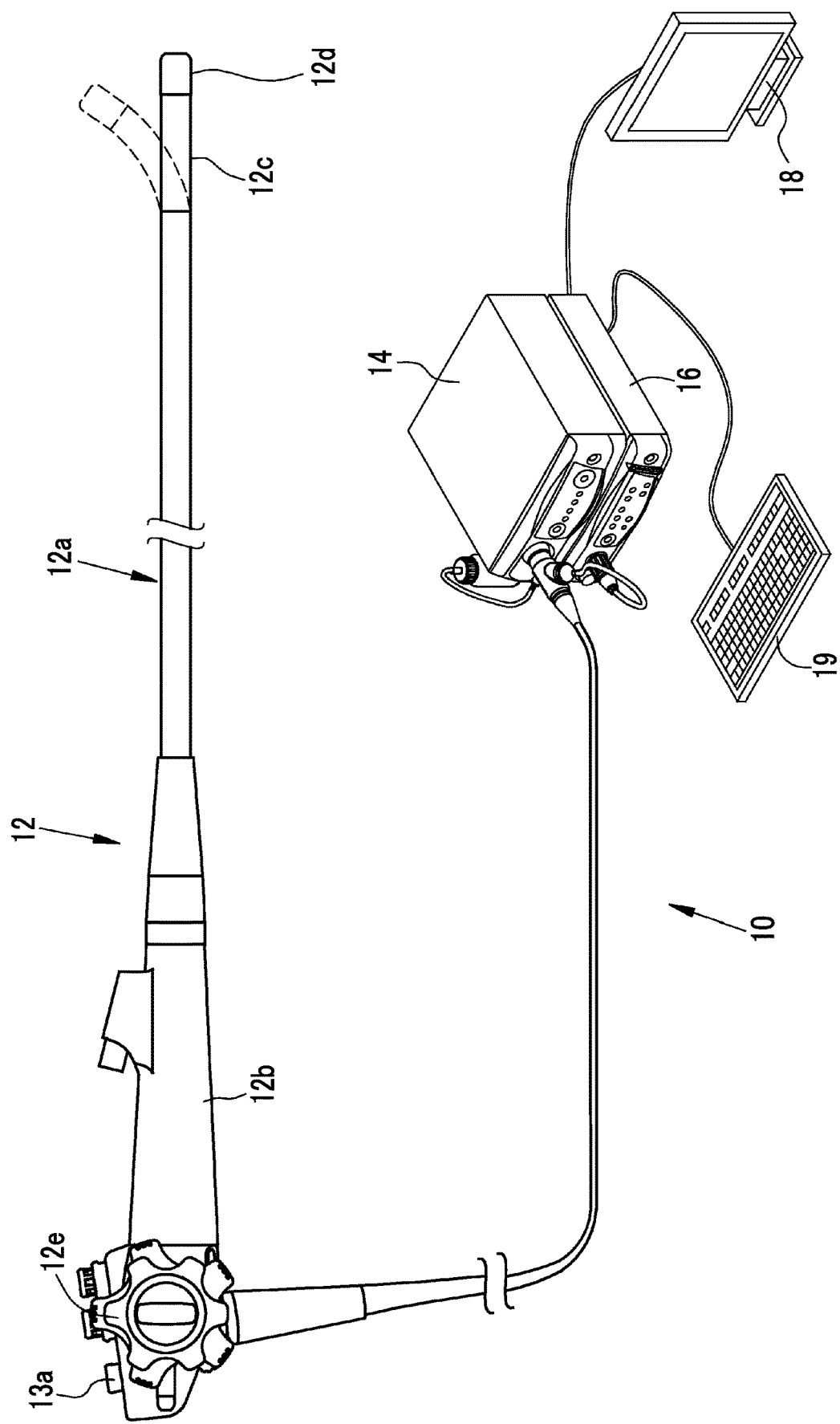
FIG. 1 is a diagram showing the appearance of an endoscope system according to a first embodiment.

As shown in FIG. 1, an endoscope system 10 according to a first embodiment includes an endoscope 12, a light source device 14, a processor device 16, a monitor 18, and a user interface 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d is made to face in a desired direction.

Further, the operation part 12b is provided with a mode changeover SW 13a in addition to the angle knobs 12e. The mode changeover SW 13a is used for an operation for switching a normal observation mode and a fluorescence observation mode. The normal observation mode is a mode where a normal image is displayed on the monitor 18. The fluorescence observation mode is a mode where a fluorescence image is displayed on the monitor 18. A foot switch (not shown) may be used as a mode switching unit, which is used to switch a mode, other than the mode changeover SW 13a.

The processor device 16 is electrically connected to the monitor 18 and the user interface 19. The monitor 18 outputs and displays image information and the like. The user interface 19 includes a keyboard, a mouse, and the like, and has a function to receive an input operation, such as function settings. An external recording unit (not shown), which records image information and the like, may be connected to the processor device 16.

Figure 2:
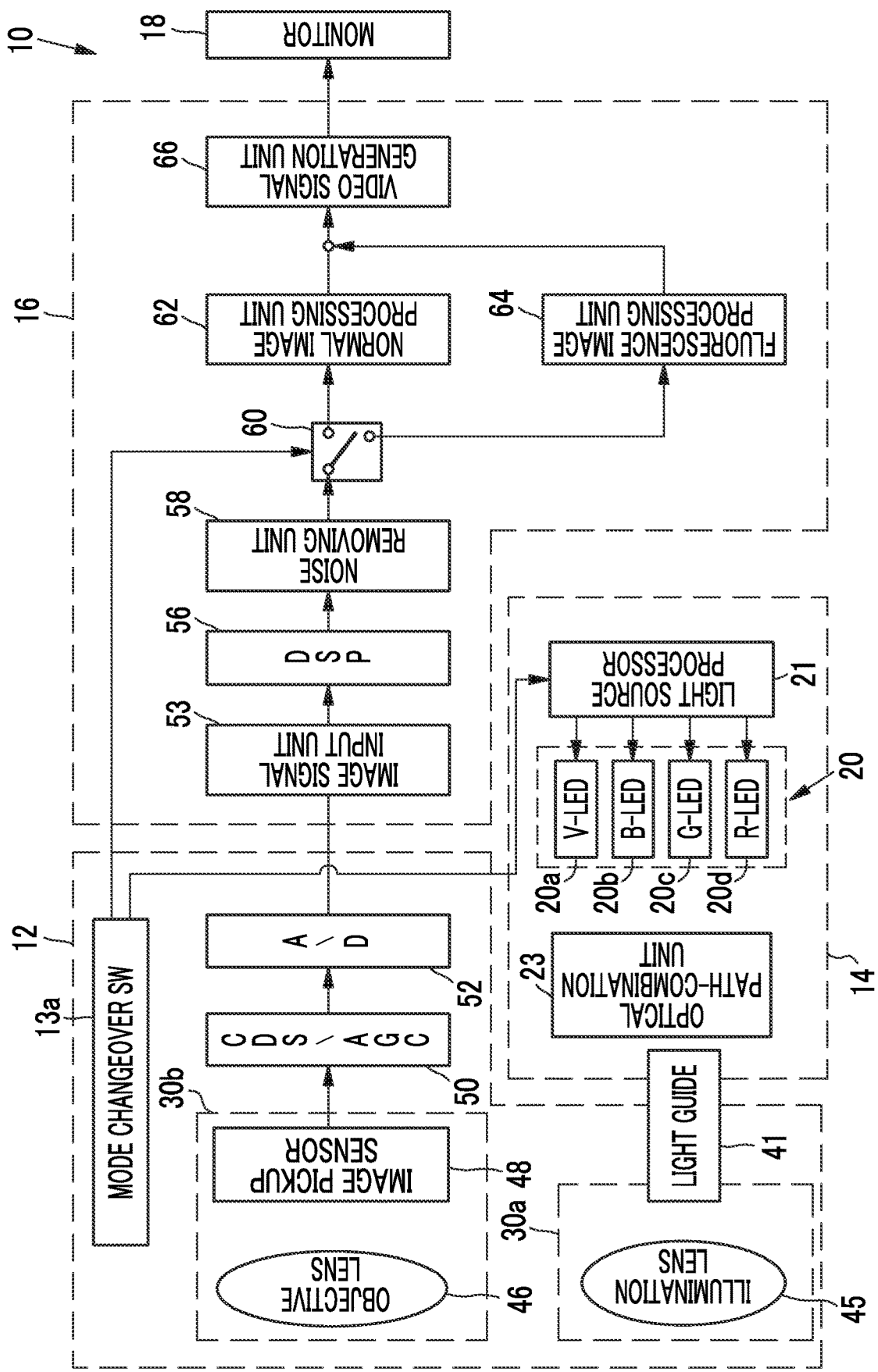
FIG. 2 is a block diagram showing the functions of the endoscope system according to the first embodiment.

As shown in FIG. 2, the light source device 14 comprises: a light source unit 20 that includes a violet light emitting diode (V-LED) 20a, a blue light emitting diode (B-LED) 20b, a green light emitting diode (G-LED) 20c, and a red light emitting diode (R-LED) 20d; a light source processor 21 that controls the drive of the four color LEDs 20a to 20d; and an optical path-combination unit 23 that combines the optical paths of four types of color light that are emitted from the four color LEDs 20a to 20d. The inside of an object to be examined is irradiated with the pieces of light, which are combined by the optical path-combination unit 23, through a light guide 41 inserted into the insertion part 12a and an illumination lens 45. A laser diode (LD) may be used instead of the LED.

Figure 3:
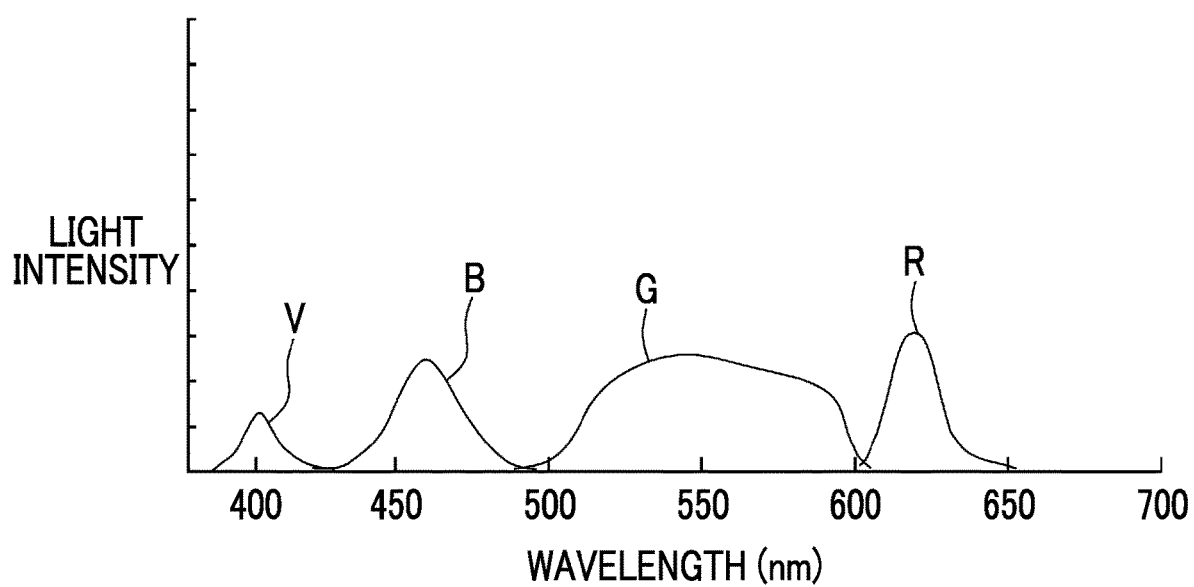
FIG. 3 is a graph showing the emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

In the fluorescence observation mode, blue light B, green light G, and red light R are used as reference light that has at least a wavelength range from a blue-light wavelength range to a green-light wavelength range and violet light V is used as excitation light that excites a drug contained in an object to be observed to cause chemical fluorescence to be emitted. A drug having an affinity for a lesion area, such as cancer, is used as the drug. In this case, it is preferable that 5-ALA is used as the drug in a case where violet light V is used as excitation light. It is preferable that excitation light in a red-light wavelength range is used in a case where Laserphyrin is used as the drug. Further, it is preferable that excitation light in a blue-light wavelength range is used in a case where fluorescein or Rhodamine Green is used as the drug. Furthermore, it is preferable that excitation light in a green-light wavelength range is used in a case where SYPRO RED is used as the drug.

The light source processor 21 turns on the V-LED 20a, the B-LED 20b, the G-LED 20c, and the R-LED 20d in the normal observation mode. Accordingly, the object to be observed is irradiated with light in which four types of color light, that is, violet light V, blue light B, green light G, and red light R are mixed, as normal light. Further, the light source processor 21 controls the respective LEDs 20a to 20d so that the light amount ratios of violet light V, blue light B, green light G, and red light R are Vc:Bc:Gc:Rc in the normal observation mode. On the other hand, the light source processor 21 controls the respective LEDs 20a to 20d so that the light amount ratios of violet light V, blue light B, green light G, and red light R are Vs:Bs:Gs:Rs in the fluorescence observation mode.

Figure 4:
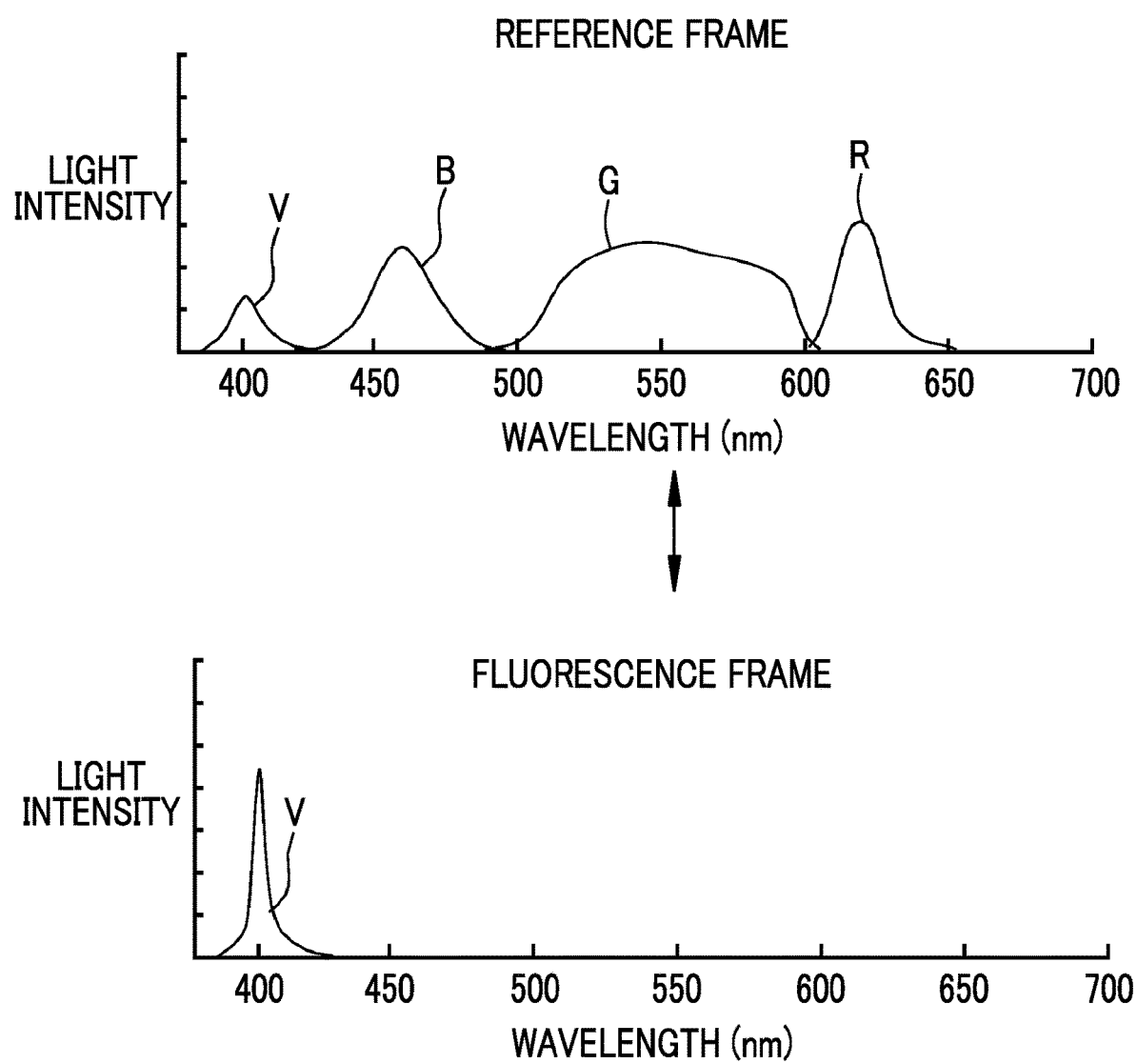
FIG. 4 is a diagram showing a reference frame and a fluorescence frame.

The light source processor 21 performs a control to switch a reference frame where excitation light and reference light are emitted and a fluorescence frame where only excitation light is emitted at a specific number of frames in the fluorescence observation mode. Specifically, the light source processor 21 emits violet light V, blue light B, green light G, and red light R as excitation light and reference light by turning on the V-LED 20a, the B-LED 20b, the G-LED 20c, and the R-LED 20d at the reference frame as shown in FIG. 4. Further, the light source processor 21 emits violet light V as excitation light by turning on only the V-LED 20a at the fluorescence frame. In the fluorescence observation mode, the V-LED 20a, the B-LED 20b, the G-LED 20c, and the R-LED 20d may be constantly turned on without the division of the reference frame and the fluorescence frame.

Figure 5:
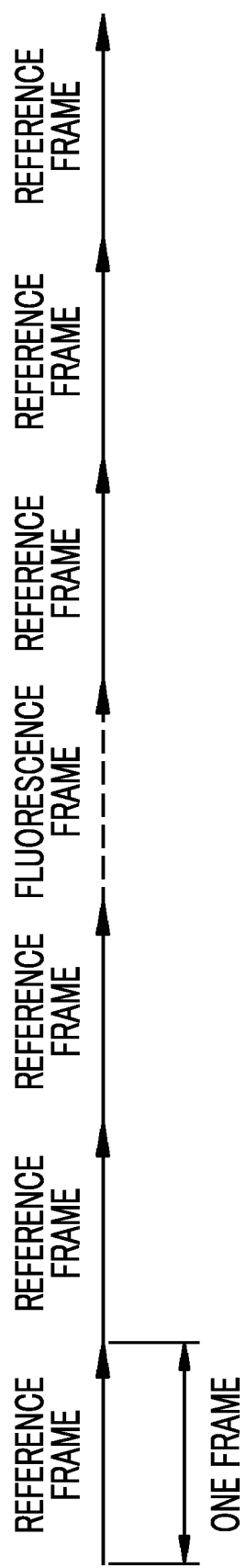
FIG. 5 is a diagram illustrating a specific number of frames.

With regard to the specific number of frames, it is preferable that the number of reference frames is set to be equal to or larger than the number of fluorescence frames. For example, it is preferable that the number of reference frames is set to three and the number of fluorescence frames is set to one as the specific number of frames as shown in FIG. 5. Further, it is preferable that the minimum number of fluorescence frames is one in a case where an image pickup sensor 48 uses a global shutter system (CCD), and it is preferable that the minimum number of fluorescence frames is two in a case where the image pickup sensor 48 uses a rolling shutter system (CMOS). The reference frame and the fluorescence frame are automatically switched in this embodiment. However, only the reference frame may be continuously displayed as long as a user does not perform a switching operation, and the reference frame may be switched to the fluorescence frame in a case where a user performs a switching operation.

In this specification, the light amount ratios include a case where the ratio of at least one semiconductor light source is 0 (zero). Accordingly, the light amount ratios include a case where any one or two or more of the respective semiconductor light sources are not turned on. For example, even though only one semiconductor light source is turned on and the other three semiconductor light sources are not turned on as in a case where the light amount ratios of violet light V, blue light B, green light G, and red light R are 1:0:0:0, it is regarded that the light source unit 20 has light amount ratios.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 µm, a cladding diameter of 125 µm, and a protective layer forming a covering is in the range of φ 0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and the image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the embodiment of the present invention is a color image pickup sensor that is used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

In the case of the normal observation mode, the image pickup sensor 48 outputs normal image signals by picking up the image of an object to be observed that is illuminated with normal light. Further, in the case of the fluorescence observation mode, the image pickup sensor 48 outputs fluorescence and reference image signals by picking up the image of an object to be observed that is illuminated with excitation light and reference light at the reference frame. Furthermore, the image pickup sensor 48 outputs fluorescence image signals, which include the components of chemical fluorescence excited and emitted from an object to be observed, by picking up the image of the object to be observed that is illuminated with excitation light at the fluorescence frame.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source processor 21 causes blue light B, green light G, and red light R to be emitted in a time-sharing manner, demosaicing needs to be added to the processing of image pickup signals.

The image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals having passed through the CDS/AGC circuit 50 are converted into digital image signals by an analog/digital converter (A/D converter) 52. The digital image signals, which have been subjected to A/D conversion, are input to the processor device 16.

In the processor device 16, programs related to various types of processing are incorporated into a program memory. The processor device 16 is provided with a central controller that is formed of an image control processor. The programs incorporated into the program memory are executed by the central controller, so that the functions of an image signal input unit 53, a digital signal processor (DSP) 56, a noise removing unit 58, a signal switching unit 60, a normal image processing unit 62, a fluorescence image processing unit 64, and a video signal generation unit 66 are realized. Digital image signals obtained from the endoscope 12 are input to the image signal input unit 53.

The DSP 56 performs various types of signal processing, such as defect correction processing, offset processing, gain processing, matrix processing, gamma transformation processing, and demosaicing processing, on the received image signals. Signals of defective pixels of the image pickup sensor 48 are corrected in the defect correction processing. Dark current components are removed from the image signals subjected to the defect correction processing in the offset processing, so that an accurate zero level is set. The image signals subjected to the offset processing are multiplied by a specific gain in the gain processing, so that signal levels are adjusted. The gain processing varies depending on the normal observation mode and the fluorescence observation mode. With regard to the gain processing in the normal observation mode, R-image signals, G-image signals, and B-image signals of the normal image signals are multiplied by an R-gain coefficient, a G-gain coefficient, and a B-gain coefficient for normal observation, respectively. With regard to the gain processing in the fluorescence observation mode, R-image signals, G-image signals, and B-image signals of the fluorescence and reference image signals are multiplied by an R-gain coefficient, a G-gain coefficient, and a B-gain coefficient for fluorescence observation, respectively.

The matrix processing for improving color reproducibility is performed on the image signals subjected to the gain processing. The matrix processing varies depending on the normal observation mode and the fluorescence observation mode. With regard to the matrix processing in the normal observation mode, matrix processing for normal observation is performed on the normal image signals. With regard to the matrix processing in the fluorescence observation mode, matrix processing for fluorescence observation is performed on the fluorescence and reference image signals.

After that, brightness or chroma saturation is adjusted by the gamma transformation processing. The demosaicing processing (also referred to as equalization processing or demosaicing) is performed on the image signals subjected to the matrix processing, so that signals of colors deficient in each pixel are generated by interpolation. All the pixels are made to have the signals corresponding to the respective colors of R, G, and B by this demosaicing processing.

The noise removing unit 58 performs noise removal processing (for example, a moving-average method, a median filtering method, or the like) on the image signals, which have been subjected to gamma correction and the like by the DSP 56, to remove noise from the image signals. The image signals from which noise has been removed are transmitted to the signal switching unit 60.

In a case where a mode is set to the normal observation mode by the mode changeover SW 13a, the signal switching unit 60 transmits the normal image signals to the normal image processing unit 62 as image signals. In a case where a mode is set to the fluorescence observation mode by the mode changeover SW 13a, the signal switching unit 60 transmits the fluorescence and reference image signals and the fluorescence image signals to the fluorescence image processing unit 64 as image signals.

The normal image processing unit 62 performs image processing for a normal image on the normal image signals. The image processing for a normal image includes structure enhancement processing for a normal image, and the like. The normal image signals, which have been subjected to the image processing for a normal image, are input to the video signal generation unit 66 from the normal image processing unit 62 as a normal image.

The fluorescence image processing unit 64 generates a fluorescence image on the basis of the fluorescence and reference image signals or the fluorescence image signals. The details of the fluorescence image processing unit 64 will be described later. The fluorescence image generated by the fluorescence image processing unit 64 is input to the video signal generation unit 66.

The video signal generation unit 66 converts the normal image or the special image, which is input from the normal image processing unit 62 or the fluorescence image processing unit 64, into video signals for displaying the image as an image that can be displayed on the monitor 18. The monitor 18 displays the normal image on the basis of the video signals.

Figure 6:
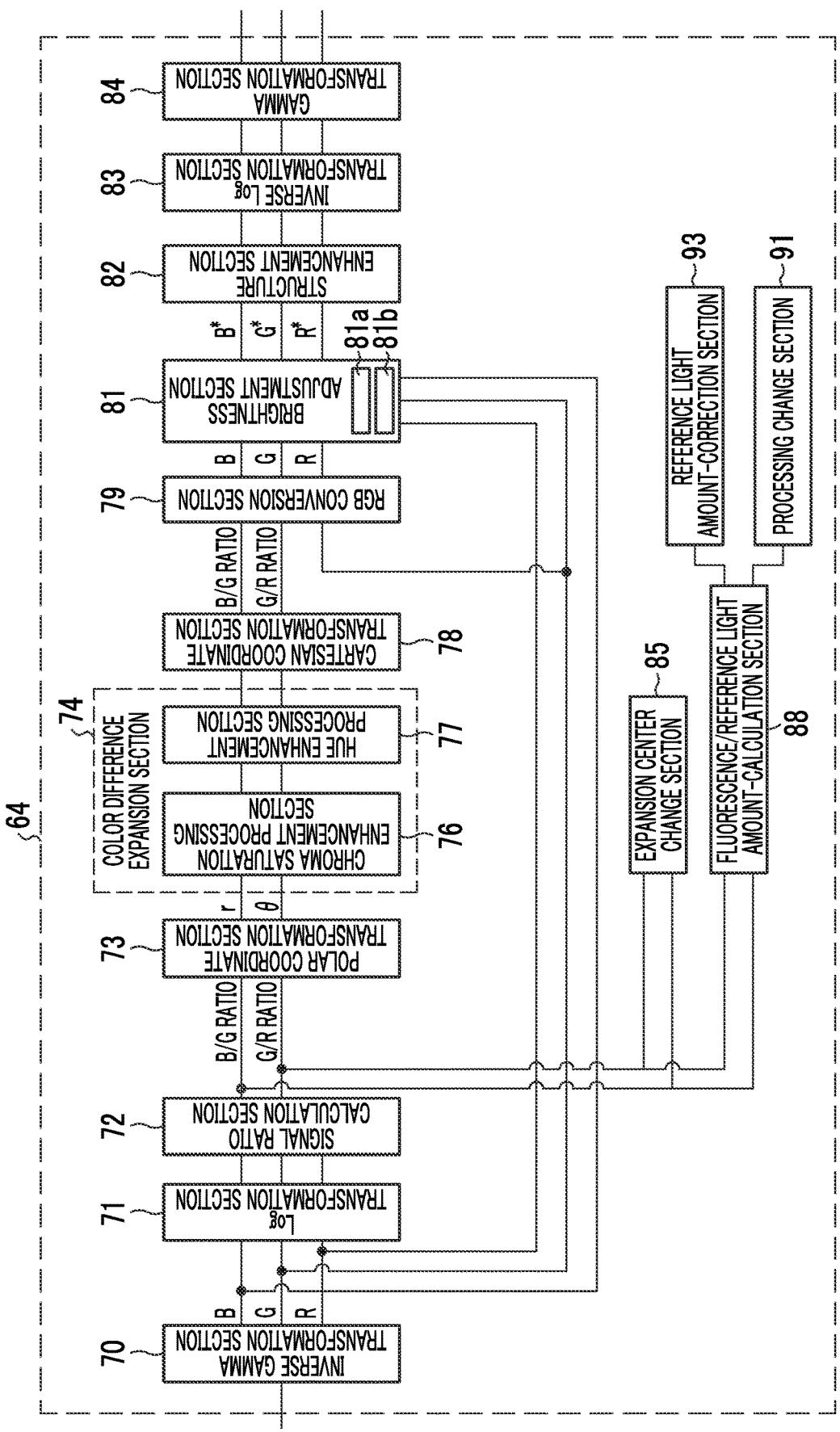
FIG. 6 is a block diagram showing the functions of a fluorescence image processing unit that is used in a case where a feature space is a signal ratio space.

As shown in FIG. 6, the fluorescence image processing unit 64 comprises an inverse gamma transformation section 70, a Log transformation section 71, a signal ratio calculation section 72, a polar coordinate transformation section 73, a color difference expansion section 74, a Cartesian coordinate transformation section 78, an RGB conversion section 79, a brightness adjustment section 81, a structure enhancement section 82, an inverse Log transformation section 83, a gamma transformation section 84, an expansion center change section 85, and a fluorescence/reference light amount-calculation section 88.

The fluorescence and reference image signals are input to the inverse gamma transformation section 70. Further, the fluorescence and reference image signals and the fluorescence image signals, which are required to change an expansion center, are input to the expansion center change section 85. Furthermore, the fluorescence and reference image signals and the fluorescence image signals, which are required to calculate the amount of fluorescence and reference light, are input to the fluorescence/reference light amount-calculation section 88. It is preferable that the fluorescence and reference image signals are RGB image signals corresponding to three colors and consisting of B-image signals output from the B-pixels of the image pickup sensor 48, G-image signals output from the G-pixels of the image pickup sensor 48, and R-image signals output from the R-pixels of the image pickup sensor 48. Further, it is preferable that the fluorescence image signals are three color image signals of RGB image signals, but the fluorescence image signals may be only image signals including the components of chemical fluorescence, for example, R-image signals in a case where the components of chemical fluorescence have a red-light wavelength range.

The inverse gamma transformation section 70 performs inverse gamma transformation on the input RGB three-channel digital image signals. Since the RGB image signals subjected to this inverse gamma transformation are linear reflectance-RGB signals that are linear in a reflectance from a sample, a ratio of signals related to a variety of biological information of the sample among the RGB image signals is high. A linear reflectance-R-image signal is referred to as a first R-image signal, a linear reflectance-G-image signal is referred to as a first G-image signal, and a linear reflectance-B-image signal is referred to as a first B-image signal. The first R-image signal, the first G-image signal, and the first B-image signal are collectively referred to as first RGB image signals.

The Log transformation section 71 performs Log transformation on each of the linear reflectance-RGB image signals. Accordingly, an R-image signal (log R) subjected to Log transformation, a G-image signal (log G) subjected to Log transformation, and a B-image signal (log B) subjected to Log transformation are obtained. The signal ratio calculation section 72 (corresponding to "color information acquisition section" of the present invention) calculates a B/G ratio (a value obtained after "−log" is omitted from −log(B/G) is written as "B/G ratio") by performing differential processing (log G−log B=log G/B=−log (B/G)) on the basis of the G-image signal and the B-image signal subjected to Log transformation. Further, the signal ratio calculation section 72 calculates a G/R ratio by performing differential processing (log R−log G=log R/G=−log (G/R)) on the basis of the R-image signal and the G-image signal subjected to Log transformation. Like the B/G ratio, a value obtained after "−log" is omitted from −log (G/R) is referred to as "G/R ratio".

The B/G ratio and the G/R ratio are obtained for each pixel from the pixel values of pixels that are present at the same positions in the B-image signals, the G-image signals, and the R-image signals. Further, the B/G ratio and the G/R ratio are obtained for each pixel. Furthermore, the B/G ratio correlates with a blood vessel depth (a distance between the surface of a mucous membrane and the position of a specific blood vessel). Accordingly, in a case where a blood vessel depth varies, the B/G ratio is also changed with a variation in blood vessel depth. Moreover, the G/R ratio correlates with the amount of blood (hemoglobin index). Accordingly, in a case where the amount of blood is changed, the G/R ratio is also changed with a variation in the amount of blood.

The polar coordinate transformation section 73 transforms the B/G ratio and the G/R ratio, which are obtained from the signal ratio calculation section 72, into a radius vector r and an angle θ. In the polar coordinate transformation section 73, the transformation of the B/G ratio and the G/R ratio into the radius vector r and the angle θ are performed for all the pixels. The color difference expansion section 74 expands a color difference between a normal mucous membrane, which is included in an object to be observed, and a fluorescence region, which includes chemical fluorescence excited and emitted from a drug contained in the object to be observed, in a signal ratio space (feature space) formed by the B/G ratio and the G/R ratio that are one of a plurality of pieces of color information. The expansion of a chroma saturation difference between the normal mucous membrane and the fluorescence region or the expansion of a hue difference between the normal mucous membrane and the fluorescence region is performed in this embodiment as the expansion of a color difference. For this purpose, the color difference expansion section 74 includes a chroma saturation enhancement processing section 76 and a hue enhancement processing section 77.

The chroma saturation enhancement processing section 76 performs chroma saturation enhancement processing for expanding a chroma saturation difference between the normal mucous membrane and the fluorescence region in the signal ratio space. Specifically, the chroma saturation enhancement processing is performed by the expansion or compression of the radius vector r in the signal ratio space. The hue enhancement processing section 77 performs hue enhancement processing for expanding a hue difference between the normal mucous membrane and the fluorescence region in the signal ratio space. Specifically, the hue enhancement processing is performed by the expansion or compression of the angle θ in the signal ratio space. The details of the chroma saturation enhancement processing section 76 and the hue enhancement processing section 77 having been described above will be described later.

The Cartesian coordinate transformation section 78 transforms the radius vector r and the angle θ, which have been subjected to the chroma saturation enhancement processing and the hue enhancement processing, into Cartesian coordinates. Accordingly, the radius vector r and the angle θ are transformed into the B/G ratio and the G/R ratio subjected to the expansion/compression of the angle. The RGB conversion section 79 converts the B/G ratio and the G/R ratio, which have been subjected to the chroma saturation enhancement processing and the hue enhancement processing, into second RGB image signals using at least one image signal of the first RGB image signals. For example, the RGB conversion section 79 converts the B/G ratio into a second B-image signal by performing an arithmetic operation that is based on the first G-image signal of the first RGB image signals and the B/G ratio. Further, the RGB conversion section 79 converts the G/R ratio into a second R-image signal by performing an arithmetic operation that is based on the first G-image signal of the first RGB image signals and the G/R ratio. Furthermore, the RGB conversion section 79 outputs the first G-image signal as a second G-image signal without performing special conversion. The second R-image signal, the second G-image signal, and the second B-image signal are collectively referred to as the second RGB image signals.

The brightness adjustment section 81 adjusts the pixel values of the second RGB image signals using the first RGB image signals and the second RGB image signals. The reason why the brightness adjustment section 81 adjusts the pixel values of the second RGB image signals is as follows. The brightness of the second RGB image signals, which are obtained from processing for expanding or compressing a color region by the chroma saturation enhancement processing section 76 and the hue enhancement processing section 77, may be significantly different from that of the first RGB image signals. Accordingly, the pixel values of the second RGB image signals are adjusted by the brightness adjustment section 81 so that the second RGB image signals subjected to brightness adjustment have the same brightness as the first RGB image signals.

The brightness adjustment section 81 comprises a first brightness information-calculation section 81a that obtains first brightness information Yin on the basis of the first RGB image signals, and a second brightness information-calculation section 81b that obtains second brightness information Yout on the basis of the second RGB image signals. The first brightness information-calculation section 81a calculates the first brightness information Yin according to an arithmetic expression of "kr×pixel value of first R-image signal+ kg×pixel value of first G-image signal+kb×pixel value of first B-image signal". Like the first brightness information-calculation section 81a, the second brightness information-calculation section 81b also calculates the second brightness information Yout according to the same arithmetic expression as described above. In a case where the first brightness information Yin and the second brightness information Yout are obtained, the brightness adjustment section 81 adjusts the pixel values of the second RGB image signals by performing arithmetic operations that are based on the following equations (E1) to (E3).

$$R^{*} = \text{pixel value of second } R\text{-image signal} \times Yin/Yout \qquad (E1):$$

$$G^{*} = \text{pixel value of second } G\text{-image signal} \times Yin/Yout \qquad (E2):$$

$$B^{*} = \text{pixel value of second } B\text{-image signal} \times Yin/Yout \qquad (E3):$$

"R*" denotes the second R-image signal subjected to brightness adjustment, "G*" denotes the second G-image signal subjected to brightness adjustment, and "B*" denotes the second B-image signal subjected to brightness adjustment. Further, "kr", "kg", and "kb" are arbitrary constants that are in the range of "0" to "1".

The structure enhancement section 82 performs structure enhancement processing on the second RGB image signals having passed through the RGB conversion section 79. Frequency filtering or the like is used as the structure enhancement processing. The inverse Log transformation section 83 performs inverse Log transformation on the second RGB image signals having passed through the structure enhancement section 82. Accordingly, second RGB image signals having anti-logarithmic pixel values are obtained. The gamma transformation section 84 performs gamma transformation on the RGB image signals having passed through the inverse Log transformation section 83. Accordingly, second RGB image signals having gradations suitable for an output device, such as the monitor 18, are obtained. The second RGB image signals having passed through the gamma transformation section 84 are transmitted to the video signal generation unit 66.

Figure 7:
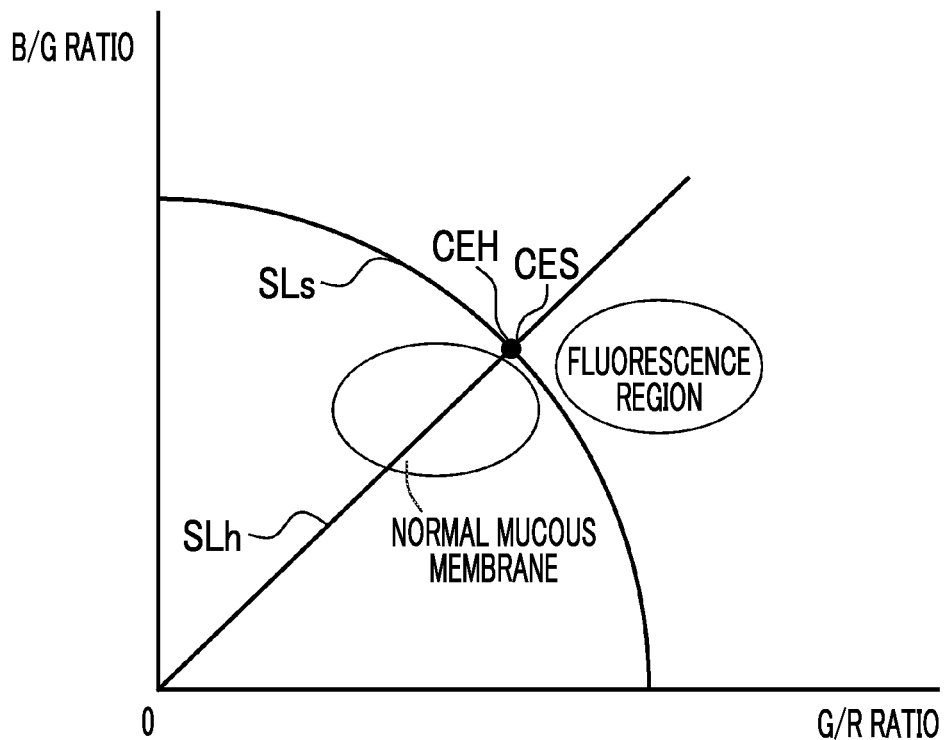
FIG. 7 is a diagram illustrating a normal mucous membrane and a fluorescence region in a signal ratio space.

The chroma saturation enhancement processing section 76 and the hue enhancement processing section 77 increase a chroma saturation difference or a hue difference between a normal mucous membrane and a fluorescence region that are distributed in a first quadrant of the signal ratio space (feature space) formed by the B/G ratio and the G/R ratio as shown in FIG. 7. Since the fluorescence region is reddish, the fluorescence region is positioned on the right side of the normal mucous membrane in the first quadrant of the signal ratio space. In a situation where the normal mucous membrane and the fluorescence region are distributed in the signal ratio space as described above, the color difference expansion section 74 determines an expansion center in the signal ratio space so that a color difference between the normal mucous membrane and the fluorescence region expands. Specifically, the chroma saturation enhancement processing section 76 determines an expansion center for chroma saturation that is used to expand a chroma saturation difference between the normal mucous membrane and the fluorescence region. Further, the hue enhancement processing section 77 determines an expansion center for hue that is used to expand a hue difference between the normal mucous membrane and the fluorescence region.

Figure 8:
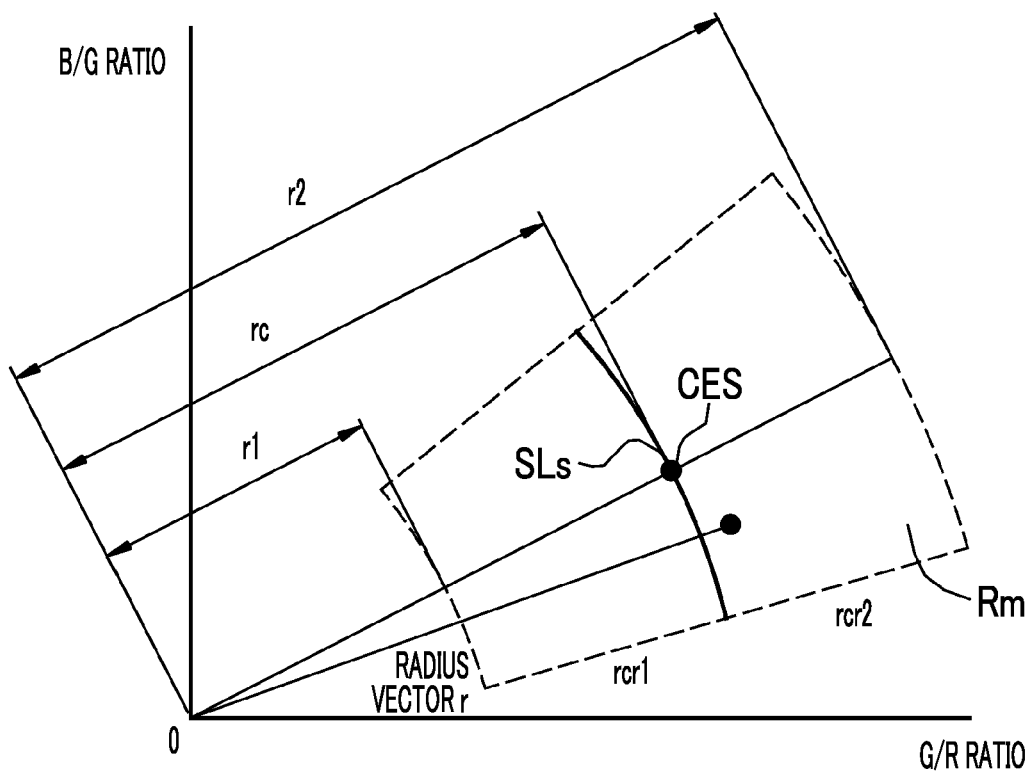
FIG. 8 is a diagram illustrating a radius vector change range Rm.

As shown in FIG. 8, the chroma saturation enhancement processing section 76 changes a radius vector r, which is represented by coordinates positioned inside a radius vector change range Rm, in the signal ratio space but does not change a radius vector r that is represented by coordinates positioned outside the radius vector change range Rm. In the radius vector change range Rm, the radius vector r is in the range of "r1" to "r2" (r1<r2). Further, an expansion center line SLs for chroma saturation is set on a radius vector rc positioned between the radius vector r1 and the radius vector r2 in the radius vector change range Rm. The expansion center line SLs for chroma saturation is provided outside a region of the normal mucous membrane (see FIG. 7). Furthermore, an expansion center CES for chroma saturation is included in the expansion center line SLs for chroma saturation.

Here, as the radius vector r is larger, chroma saturation is higher. Accordingly, a range rcr1 (r1<r<rc) in which the radius vector r is smaller than the radius vector rc represented by the expansion center line SLs for chroma saturation is defined as a low chroma saturation range. On the other hand, a range rcr2 (rc<r<r2) in which the radius vector r is larger than the radius vector rc represented by the expansion center line SLs for chroma saturation is defined as a high chroma saturation range.

Figure 9:
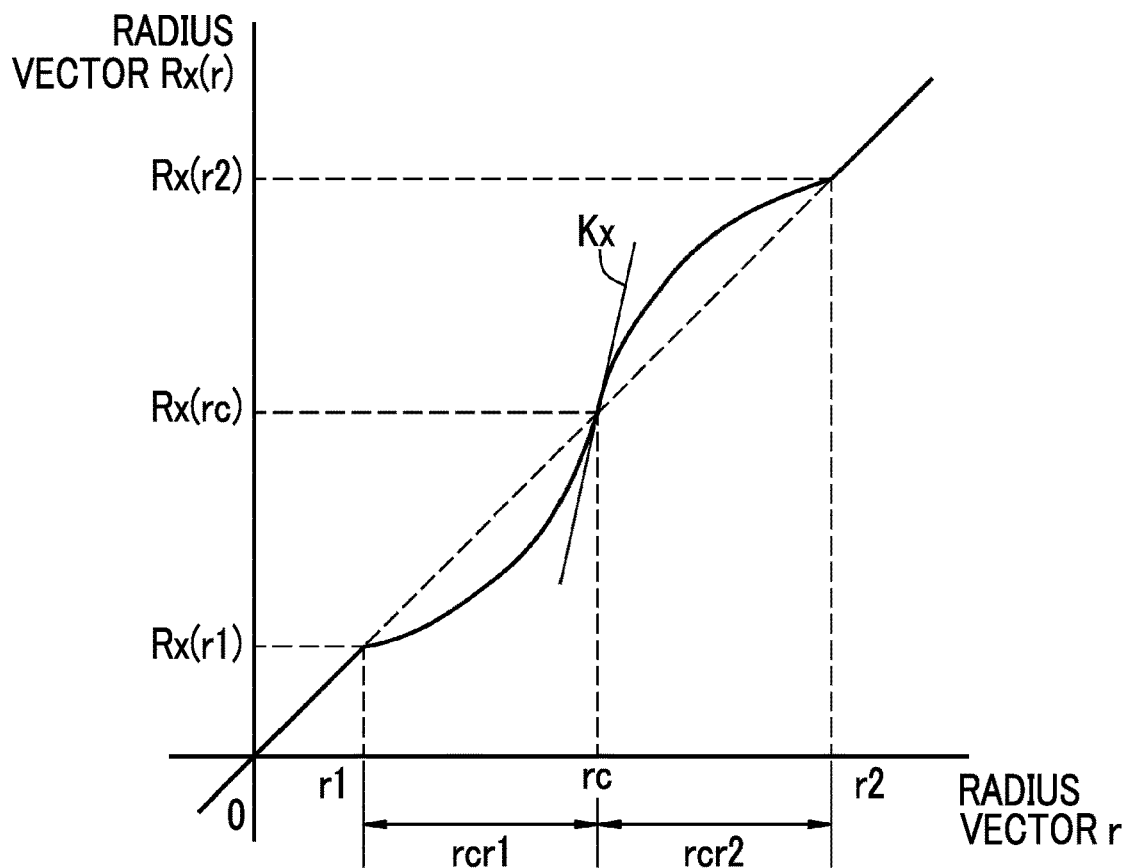
FIG. 9 is a graph showing a relationship between a radius vector r and a radius vector Rx(r) that is obtained after chroma saturation enhancement processing.

As shown in FIG. 9, the chroma saturation enhancement processing outputs a radius vector Rx(r) in response to the input of the radius vector r of coordinates included in the radius vector change range Rm. A relationship between the input and output of the chroma saturation enhancement processing is shown by a solid line. In the chroma saturation enhancement processing, an S-shaped conversion curve is used and an output value Rx(r) is made smaller than an input value r in a low chroma saturation range rcr1 but an output value Rx(r) is made larger than an input value r in a high chroma saturation range rcr2. Further, an inclination Kx of Rx(rc) is set to "1" or more. Accordingly, the chroma saturation of an object to be observed included in the low chroma saturation range can be made lower, but the chroma saturation of an object to be observed included in the high chroma saturation range can be made higher. A chroma saturation difference between a plurality of ranges to be observed can be increased by such chroma saturation enhancement processing.

Figure 10:
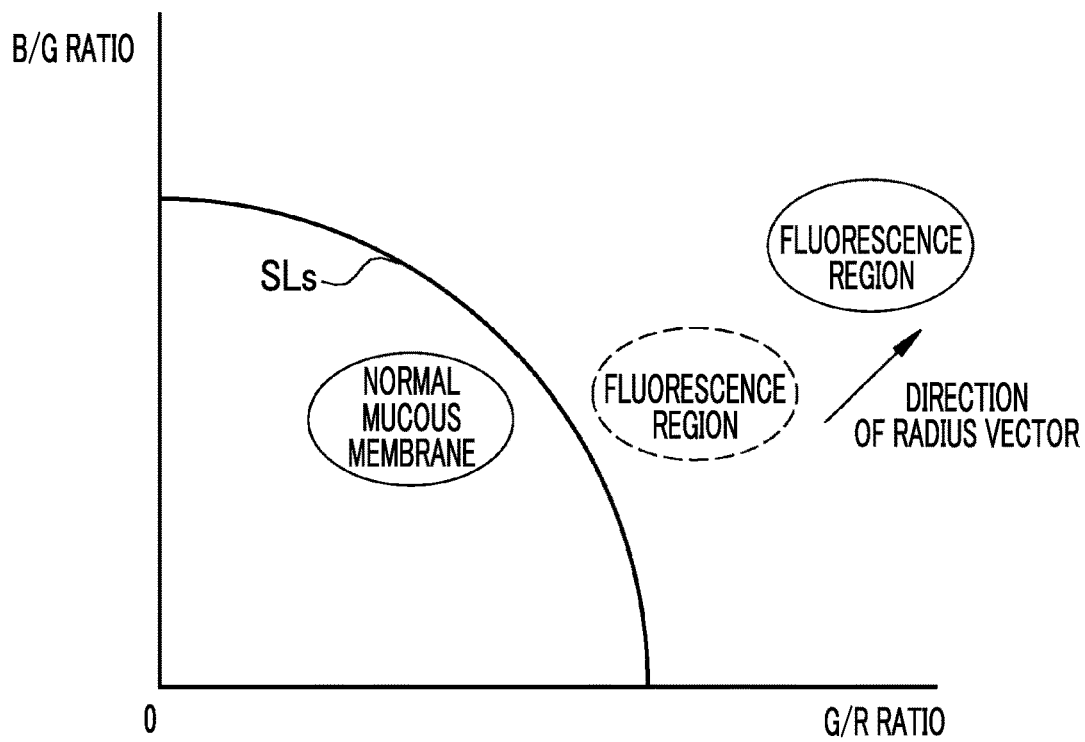
FIG. 10 is a diagram illustrating a positional relationship between fluorescence regions before and after chroma saturation enhancement processing in the signal ratio space.

In a case where the chroma saturation enhancement processing is performed as described above, a fluorescence region (solid line) subjected to the chroma saturation enhancement processing is moved to be farther from the expansion center line SLs for chroma saturation than a fluorescence region (dotted line) not yet subjected to the chroma saturation enhancement processing as shown in FIG. 10. Since the direction of a radius vector in the feature space represents the magnitude of chroma saturation, a chroma saturation difference between the fluorescence region (solid line) subjected to the chroma saturation enhancement processing and the normal mucous membrane is larger than a chroma saturation difference between the fluorescence region (dotted line) not yet subjected to the chroma saturation enhancement processing and the normal mucous membrane.

Figure 11:
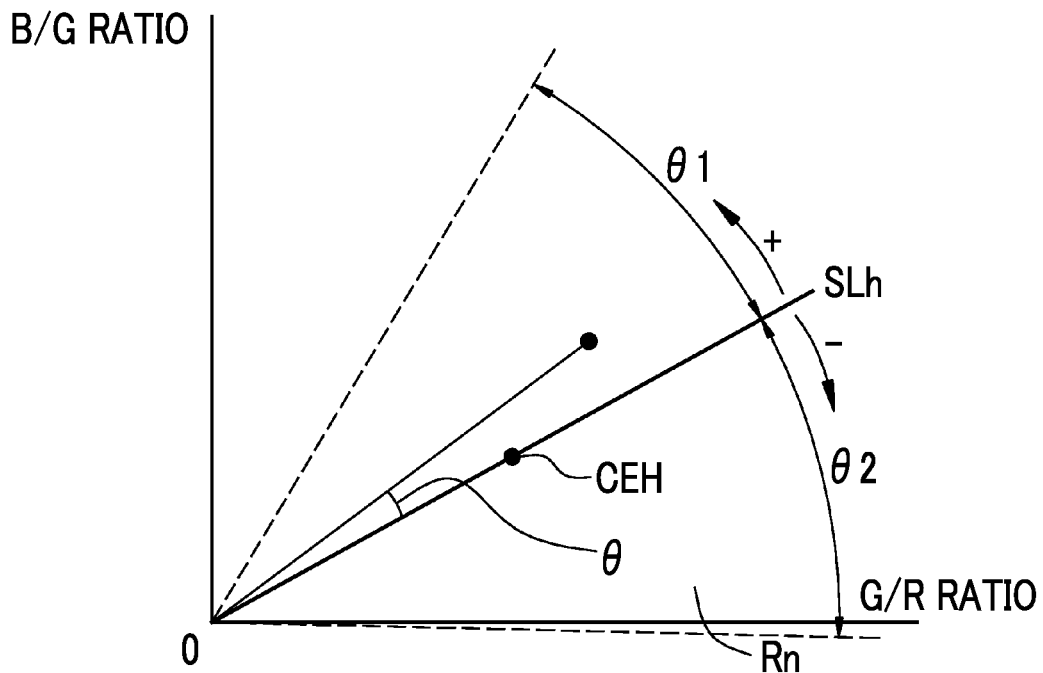
FIG. 11 is a diagram illustrating an angle change range Rn.

As shown in FIG. 11, the hue enhancement processing section 77 changes an angle θ, which is represented by coordinates positioned inside an angle change range Rn, in the signal ratio space but does not change an angle θ that is represented by coordinates positioned outside the angle change range Rn. The angle change range Rn is formed of the range of an angle θ1 in a counterclockwise direction (first hue direction) from an expansion center line SLh for hue and the range of an angle θ2 in a clockwise direction (second hue direction) from the expansion center line SLh for hue. The expansion center line SLh for hue is provided to intersect with the region of the normal mucous membrane (see FIG. 7). Further, an expansion center CEH for hue is included in the expansion center line SLh for hue.

The angle θ of coordinates included in the angle change range Rn is redefined as an angle θ from the expansion center line SLh for hue, the side of the expansion center line SLh for hue corresponding to the counterclockwise direction is defined as a positive side, and the side of the expansion center line SLh for hue corresponding to the clockwise direction is defined as a negative side. In a case where the angle θ is changed, hue is also changed. Accordingly, the range of the angle θ1 of the angle change range Rn is defined as a positive hue range θ1, and the range of the angle θ2 thereof is defined as a negative hue range θ2. It is preferable that the expansion center line SLh for hue is also a line intersecting with the range of the normal mucous membrane in the feature space like the expansion center line SLs for chroma saturation.

Figure 12:
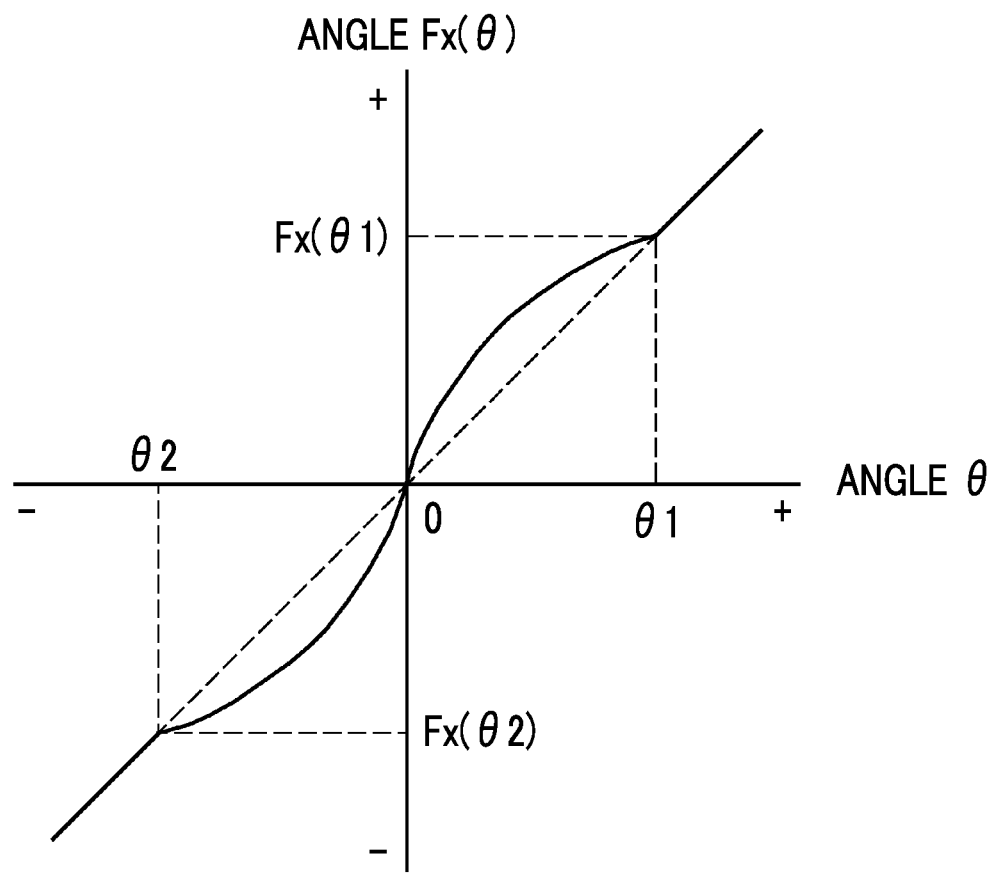
FIG. 12 is a graph showing a relationship between an angle θ and an angle Fx(θ) that is obtained after hue enhancement processing.

As shown in FIG. 12, the hue enhancement processing outputs an angle Fx(θ) in response to the input of the angle θ of coordinates included in the angle change range Rn. A relationship between the input and output of the hue enhancement processing is shown by a solid line. In the hue enhancement processing, an output Fx(θ) is made smaller than an input θ in the negative hue range θ2 but an output Fx(θ) is made larger than an input θ in the positive hue range θ1. Accordingly, a difference in hue between an object to be observed included in the negative hue range and an object to be observed included in the positive hue range can be increased.

Figure 13:
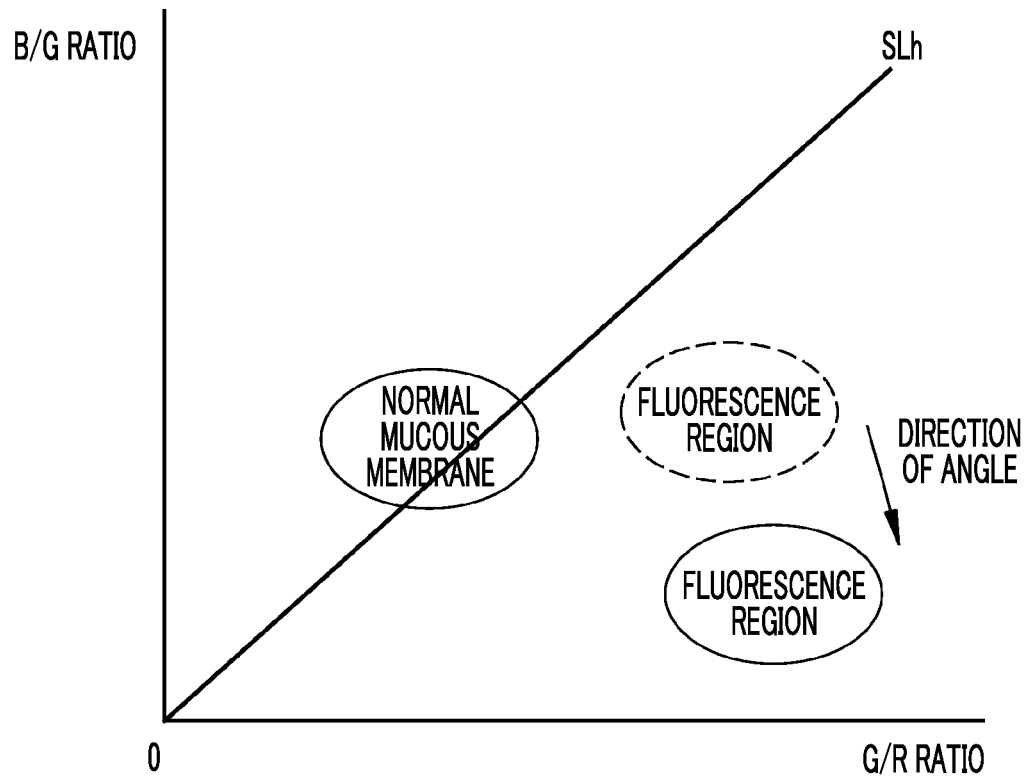
FIG. 13 is a diagram illustrating a positional relationship between fluorescence regions before and after hue enhancement processing in the signal ratio space.

In a case where the hue enhancement processing is performed as described above, a fluorescence region (solid line) subjected to the hue enhancement processing is moved to be farther from the expansion center line SLh for hue than a fluorescence region (dotted line) not yet subjected to the hue enhancement processing as shown in FIG. 13. Since the direction of an angle in the feature space represents a difference in hue, a hue difference between the fluorescence region (solid line) subjected to the hue enhancement processing and the normal mucous membrane is larger than a hue difference between the fluorescence region (dotted line) not yet subjected to the hue enhancement processing and the normal mucous membrane.

Figure 14:
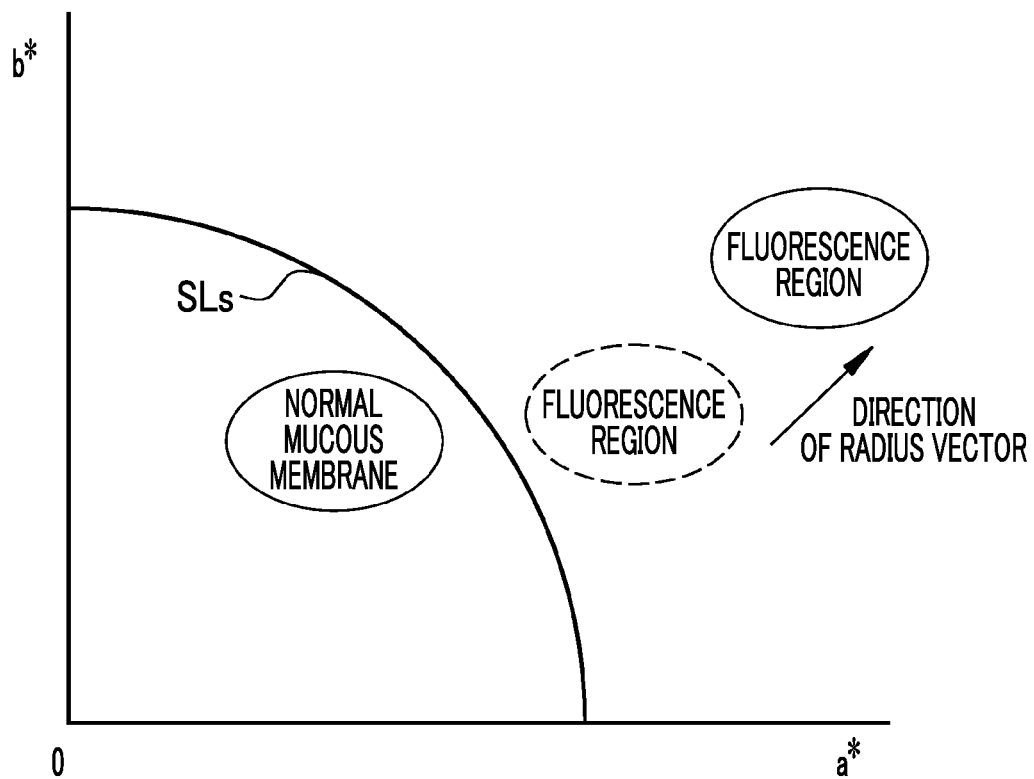
FIG. 14 is a diagram illustrating a positional relationship between fluorescence regions before and after chroma saturation enhancement processing in an ab space.
Figure 15:
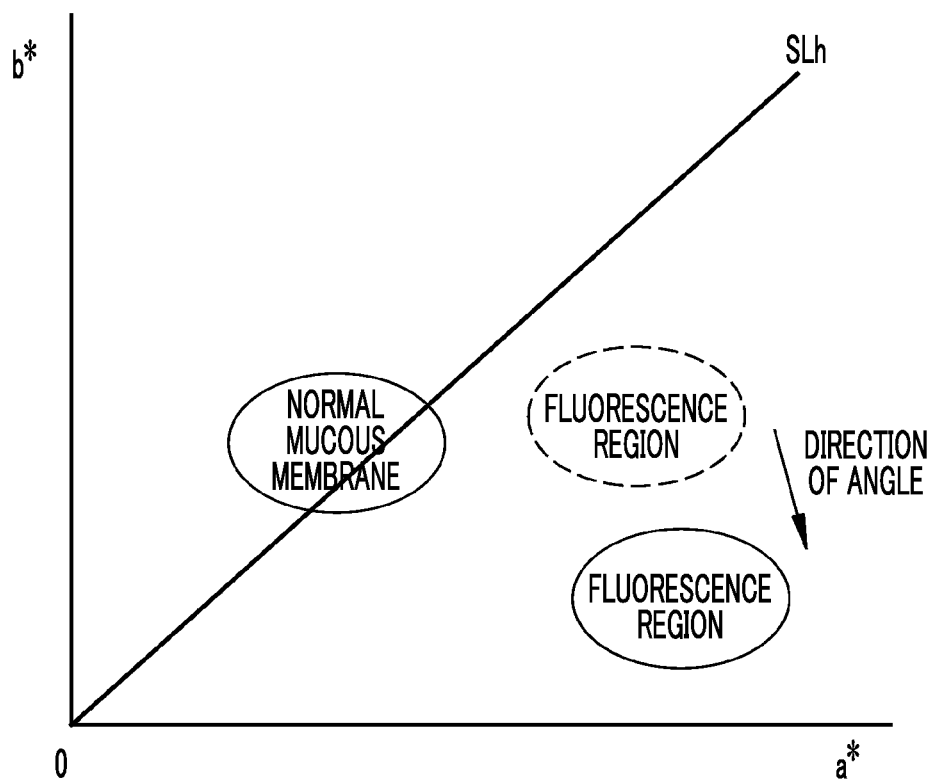
FIG. 15 is a diagram illustrating a positional relationship between fluorescence regions before and after hue enhancement processing in the ab space.

Even in the case of a feature space (ab space) formed by a* and b* (indicating the tint elements a* and b* of a CIE Lab space that are color information. The same applies hereinafter) obtained from the Lab conversion of the first RGB image signals that is performed by a Lab conversion unit, in a case where the chroma saturation enhancement processing is performed, a fluorescence region (solid line) subjected to the chroma saturation enhancement processing is moved to be farther from the expansion center line SLs for chroma saturation than a fluorescence region (dotted line) not yet subjected to the chroma saturation enhancement processing as shown in FIG. 14. Further, in a case where the hue enhancement processing is performed, a fluorescence region (solid line) subjected to the hue enhancement processing is moved to be farther from the expansion center line SLh for hue than a fluorescence region (dotted line) not yet subjected to the hue enhancement processing as shown in FIG. 15.

Figure 16:
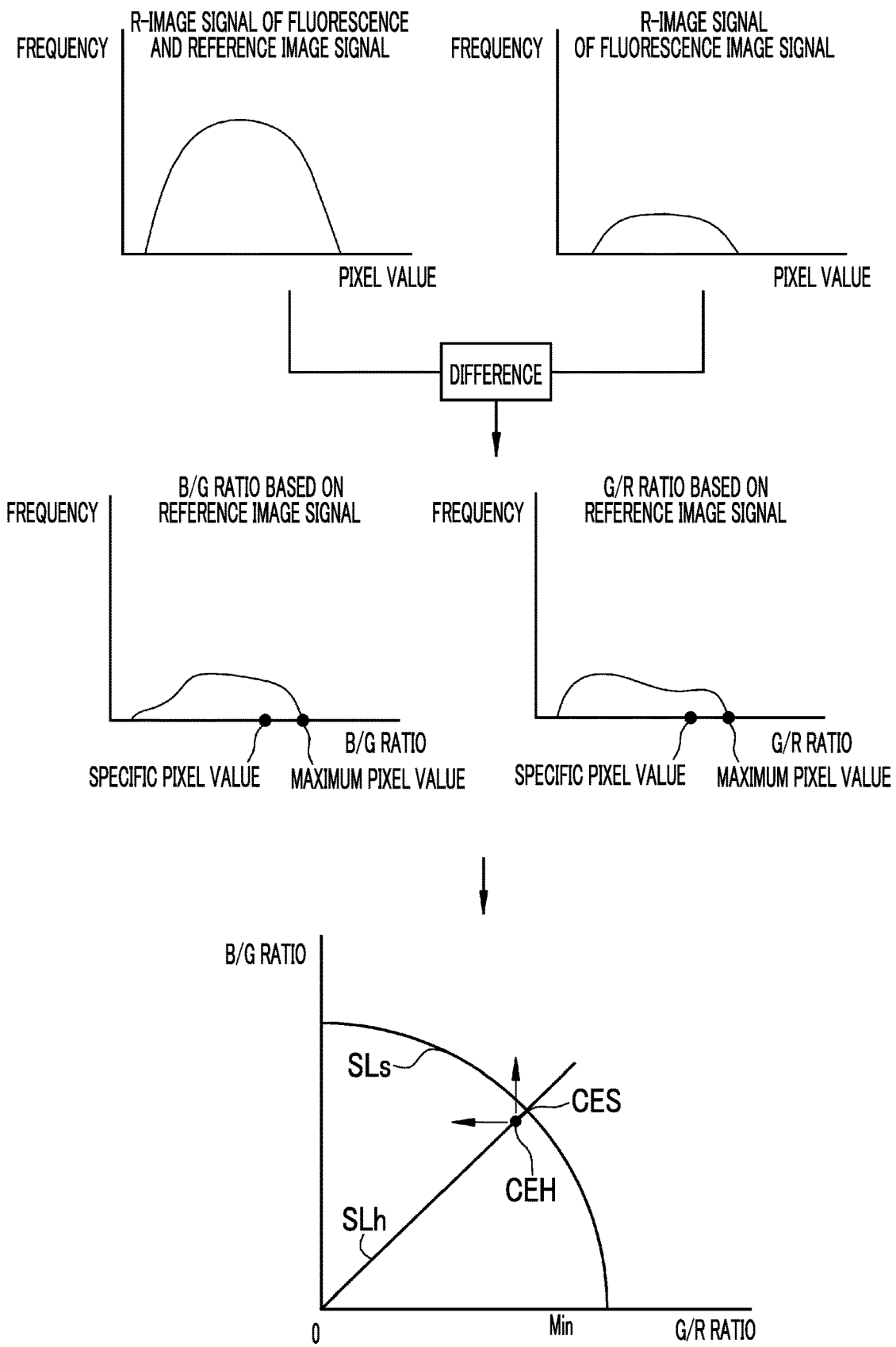
FIG. 16 is a diagram illustrating a method of calculating the amount of change of an expansion center from the frequency distribution of B/G ratios and the frequency distributions of G/R ratios based on reference image signals.

The expansion center change section 85 changes the expansion center, which is determined in the signal ratio space, on the basis of the fluorescence and reference image signals and the fluorescence image signals. Specifically, the expansion center change section 85 calculates reference image signals from differences between the fluorescence and reference image signals and the fluorescence image signals, and changes the expansion center on the basis of the calculated reference image signals. For example, the frequency distribution of B/G ratios obtained on the basis of the B-image signals and the G-image signals of the reference image signals and the frequency distribution of G/R ratios obtained on the basis of the G-image signals and the R-image signals of the reference image signals are obtained as shown in FIG. 16. Then, the amount of change of the expansion center in a vertical direction is obtained from a pixel value (specific pixel value) corresponding to a specific ratio (for example, 80%) of the maximum pixel value included in the frequency distribution of the B/G ratios. Further, the amount of change of the expansion center in a horizontal direction is obtained from a pixel value (specific pixel value) corresponding to a specific ratio (for example, 80%) of the maximum pixel value included in the frequency distribution of the G/R ratios.

For example, the expansion center change section 85 does not change the expansion center for chroma saturation or the expansion center for hue in a case where the specific pixel value is in a certain range. On the other hand, in a case where the specific pixel value is out of a certain range, the expansion center change section 85 changes the expansion center CES for chroma saturation or the expansion center CEH for hue in the vertical direction or the horizontal direction according to the amounts of change of the expansion center in the vertical direction and the horizontal direction. As the expansion center CES for chroma saturation or the expansion center CEH for hue is changed, the position of the expansion center line SLs for chroma saturation or the expansion center line SLh for hue is also changed.

Figure 17A:
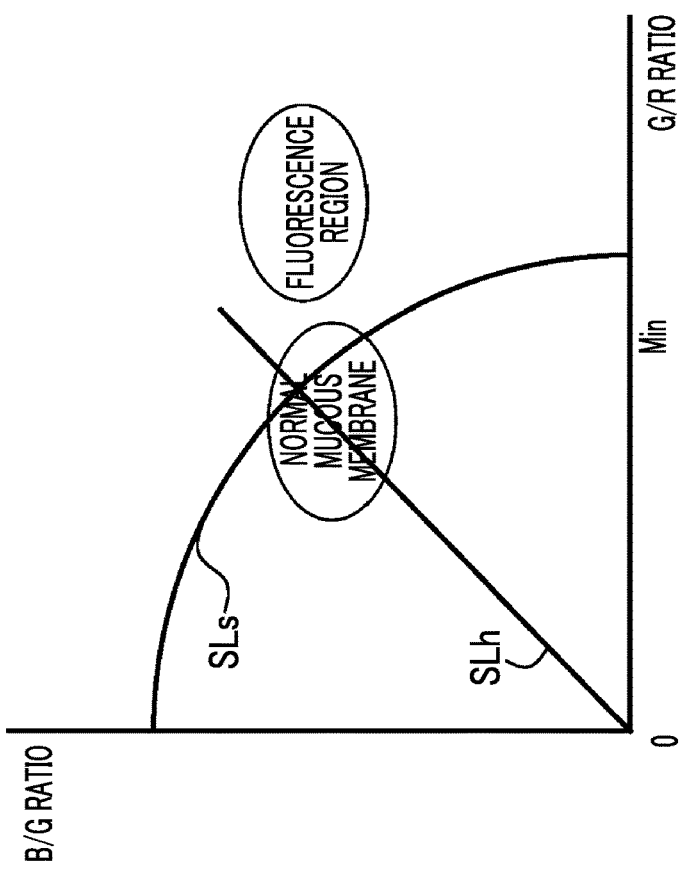
FIGS. 17A and 17B are diagrams illustrating the positions of a normal mucous membrane, a fluorescence region, and an expansion center line SLs for chroma saturation or an expansion center line SLh for hue.
Figure 17B:
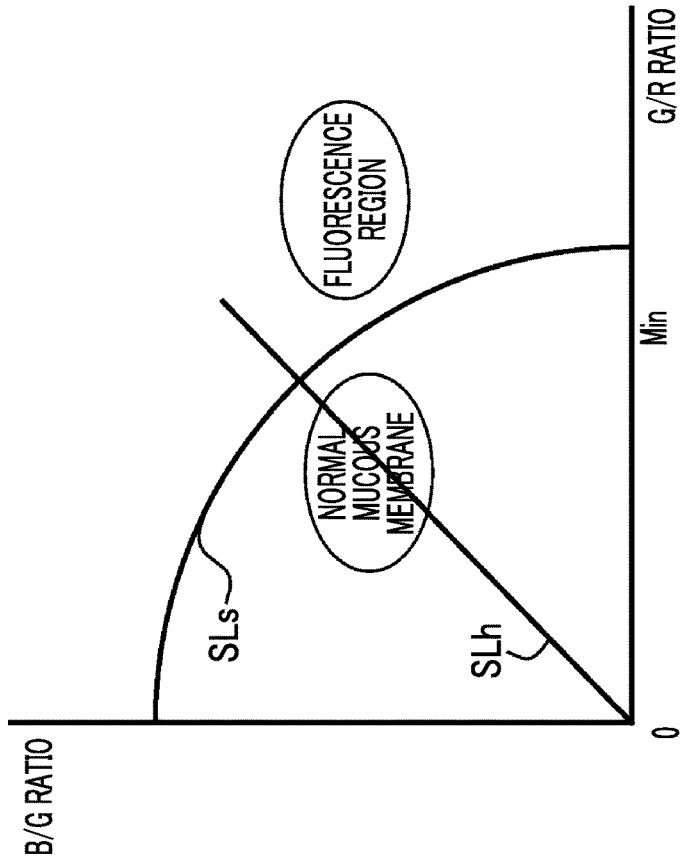

In a case where the expansion center is set to the maximum pixel values included in the frequency distributions of the B/G ratios and the G/R ratios, the positions of the normal mucous membrane and the fluorescence region and the expansion center line SLs for chroma saturation or the expansion center line SLh for hue are as shown in FIG. 17A. On the other hand, in a case where the expansion center is set to pixel values (specific pixel values) corresponding to 80% of the maximum pixel values included in the frequency distributions of the B/G ratios and the G/R ratios, the positions of the normal mucous membrane and the fluorescence region and the expansion center line SLs for chroma saturation or the expansion center line SLh for hue are as shown in FIG. 17B.

Further, the expansion center change section 85 may calculate the amount of change of the expansion center on the basis of the components of fluorescence and reference light included in the fluorescence and reference image signals and the components of fluorescence included in the fluorescence image signals. In this case, the expansion center change section 85 generates a binarized fluorescence image signal in which a fluorescence component FL and other components of the fluorescence image signal are binarized as shown in FIG. 18. In a case where the fluorescence component FL included in the binarized fluorescence image signal is equal to or lower than a threshold value for fluorescence, the expansion center change section 85 does not change the expansion center.

Figure 19:
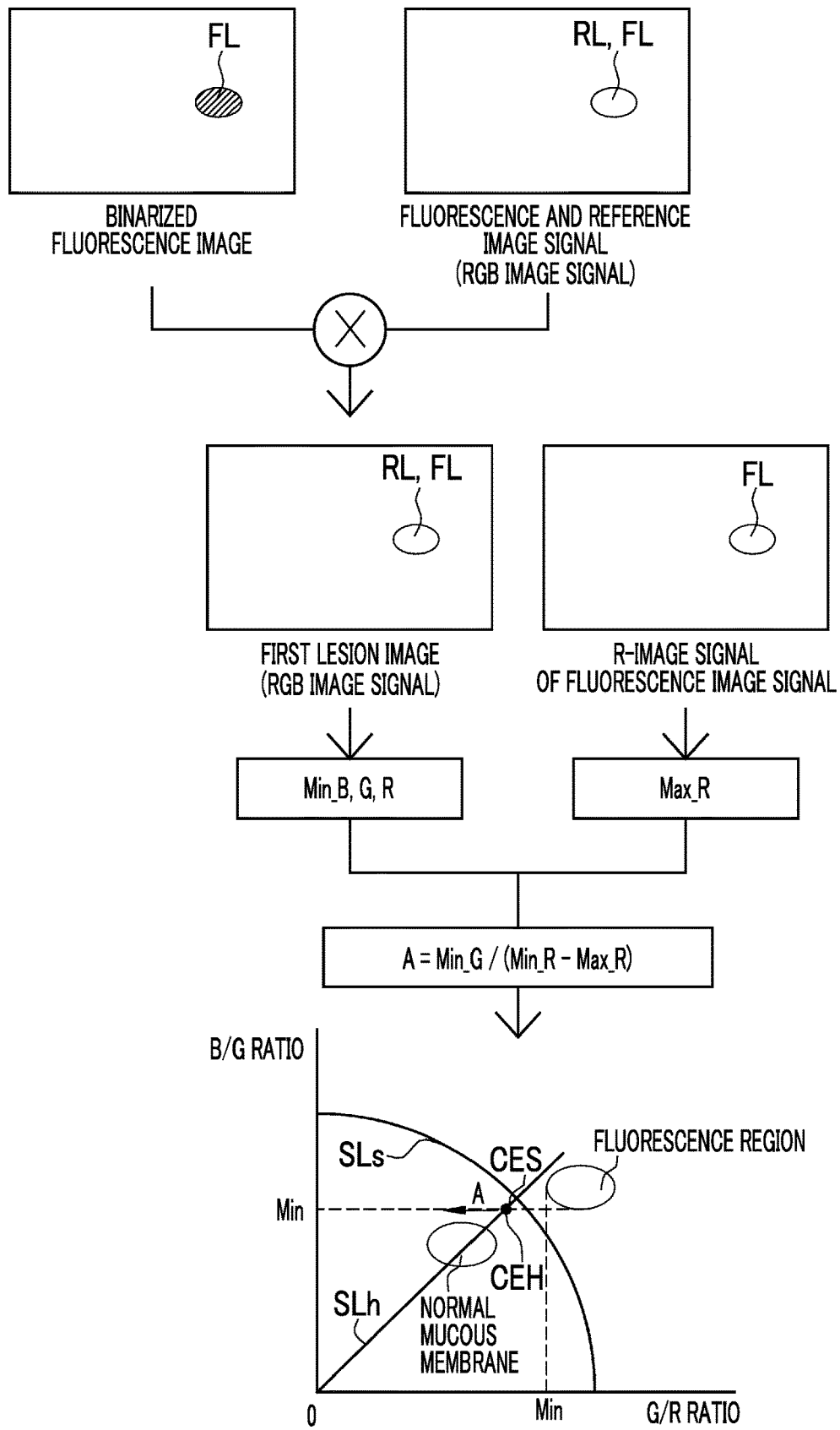
FIG. 19 is a diagram illustrating a method of calculating the amount A of change of an expansion center.

On the other hand, in a case where the fluorescence component FL exceeds the threshold value for fluorescence, the expansion center change section 85 changes the expansion center. Here, the expansion center is changed by the subtraction of the maximum amount of fluorescence to low chroma saturation side of a lesion area, or the like. As shown in FIG. 19, the expansion center change section 85 acquires a first lesion image in which a lesion area including the reference light RL and the fluorescence component FL is displayed by taking a logical product (AND) of the fluorescence and reference image signals and a binarized fluorescence image. Then, the expansion center change section 85 calculates the minimum pixel values Min_B, Min_G, and Min_R from the B-image signals, the G-image signals, and the R-image signals of the first lesion image, respectively. Further, the expansion center change section 85 calculates the maximum pixel value Max_R from the fluorescence image signals. Then, the expansion center change section 85 calculates the amount A of change of the expansion center by the following equation 1), and shifts the expansion center CES for chroma saturation or the expansion center CEH for hue in the signal ratio space in the horizontal direction by the amount A of change.

$$A = \text{Min\_G}/(\text{Min\_R} - \text{Max\_R}) \qquad \text{Equation 1)}$$

In a case where the fluorescence component FL included in the binarized fluorescence image signal exceeds the threshold value for fluorescence, the expansion center change section 85 may change the expansion center in the vertical direction and the horizontal direction of the signal ratio space as described below instead of a method of changing the expansion center in the horizontal direction of the signal ratio space. For example, the expansion center change section 85 changes the expansion center so that the expansion center is positioned on a boundary between the normal mucous membrane and a lesion area, such as the fluorescence region. Specifically, the expansion center change section 85 generates the first lesion image in which a lesion area including the components of the fluorescence and the reference light is displayed and a lesion-excluding image in which portions other than the lesion area including the components of the fluorescence and the reference light are displayed, from the fluorescence and reference image signals and the fluorescence image signals; and calculates the amount of change of the expansion center on the basis of the first lesion image and the lesion-excluding image.

Figure 20:
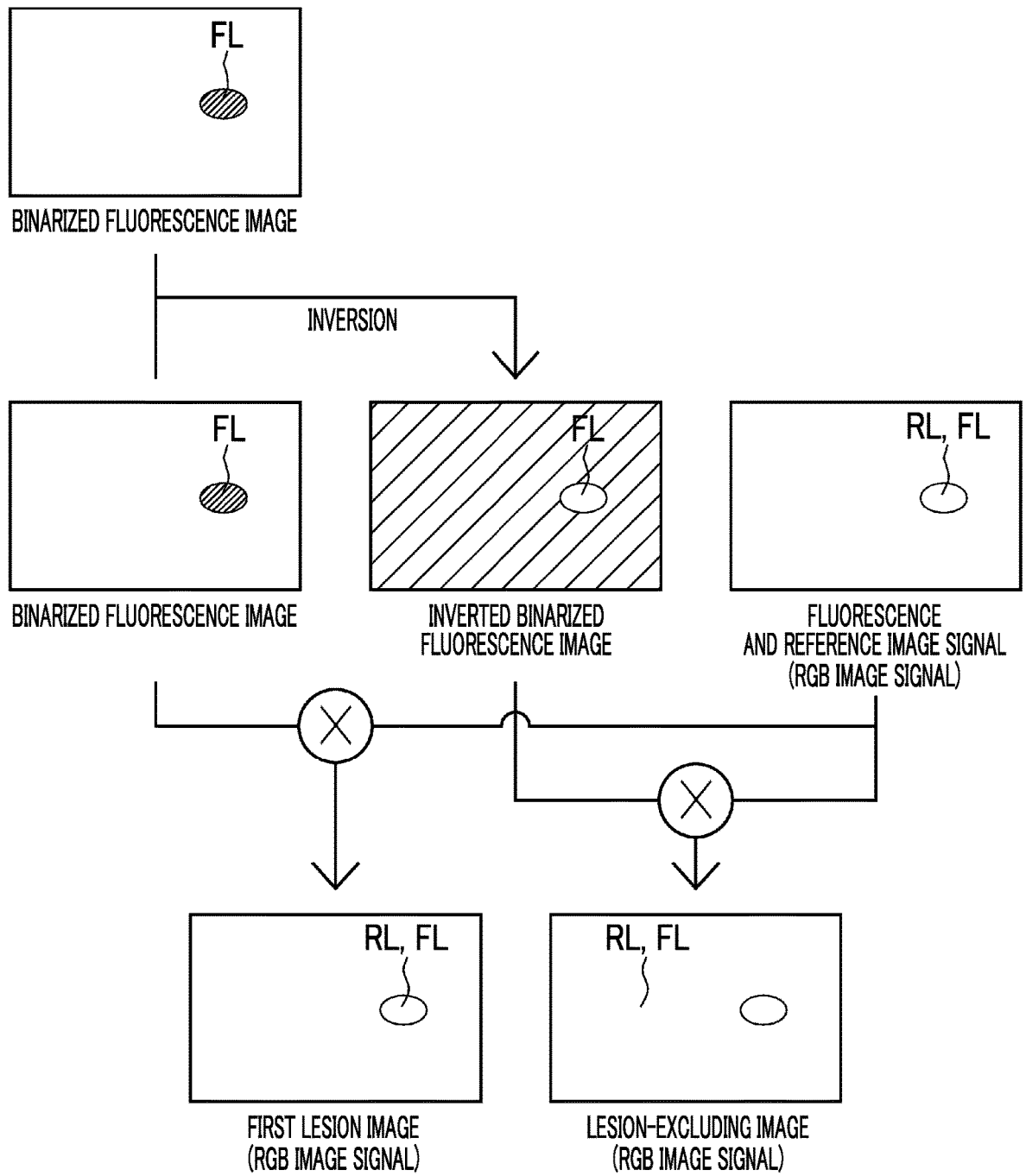
FIG. 20 is a diagram illustrating a method of generating a first lesion image and a lesion-excluding image.

In this case, as shown in FIG. 20, the expansion center change section 85 acquires the first lesion image in which the lesion area including the reference light RL and the fluorescence component FL is displayed by taking a logical product (AND) of the fluorescence and reference image signals and the binarized fluorescence image as described above. In addition to the first lesion image, the expansion center change section 85 acquires the lesion-excluding image in which portions other than the lesion area including the reference light RL and the fluorescence component FL are displayed by taking a logical product (AND) of the fluorescence and reference image signals and an inverted binarized fluorescence image in which the pixel values of the binarized fluorescence image are inverted.

Figure 21:
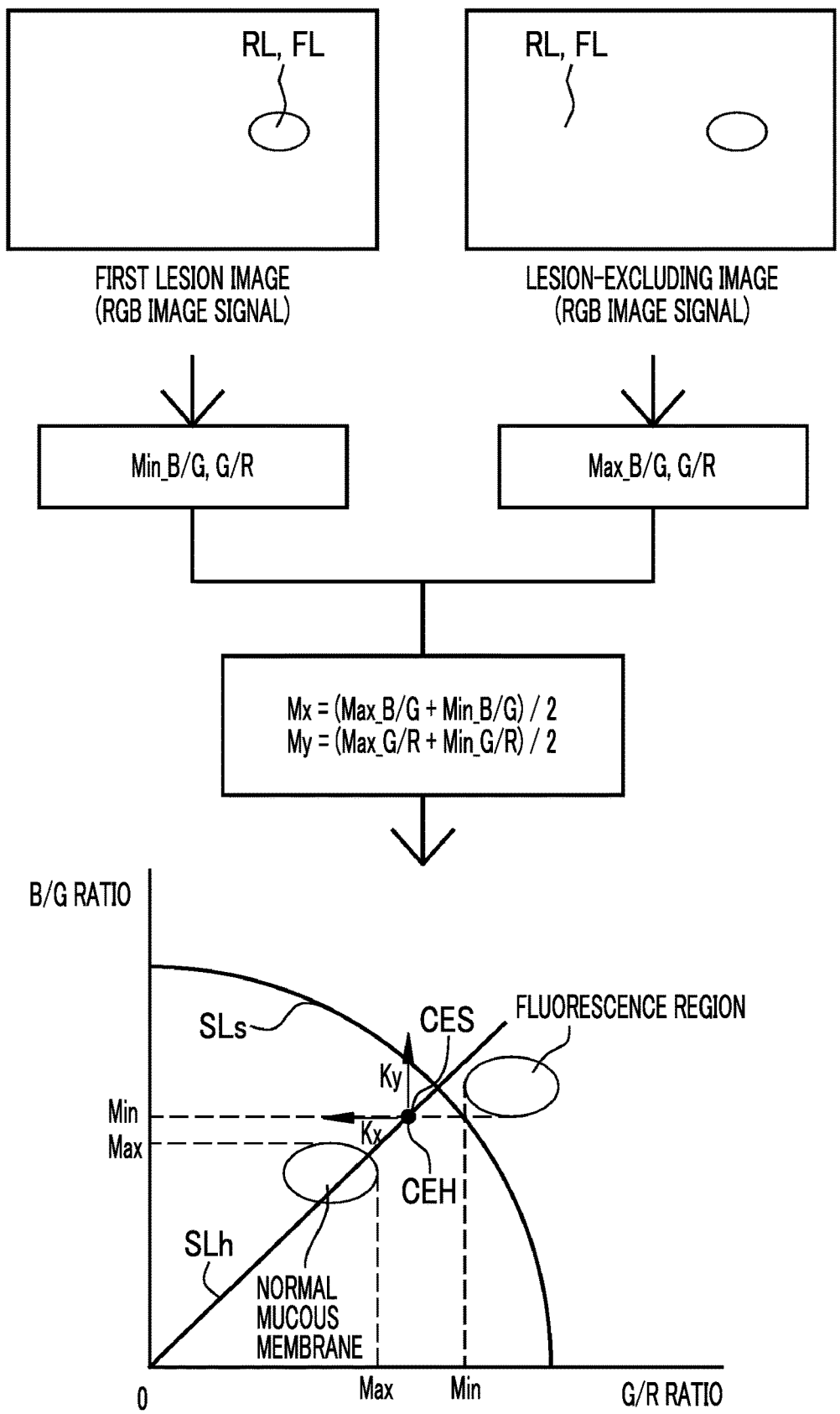
FIG. 21 is a diagram illustrating a method of calculating the amounts Mx and My of change of an expansion center.

Then, as shown in FIG. 21, the expansion center change section 85 calculates the B/G ratios and the G/R ratios of the first lesion image from the B-image signals, the G-image signals, and the R-image signals of the first lesion image and acquires Min_B/G and Min_G/R that are the minimum B/G ratio and the minimum G/R ratio among the calculated positive B/G ratios (>0) and the calculated positive G/R ratios (>0). On the other hand, the expansion center change section 85 calculates the B/G ratios and the G/R ratios of the first lesion image from the B-image signals, the G-image signals, and the R-image signals of the lesion-excluding image and acquires Max_B/G and Min_G/R that are the maximum B/G ratio and the maximum G/R ratio among the calculated B/G ratios and the calculated G/R ratios. Then, the expansion center change section 85 calculates the amount Mx of change of the expansion center in the vertical direction and the amount My of change of the expansion center in the horizontal direction by the following equation 2).

$$Mx = (Max\_B/G + Min\_B/G)/2 \qquad \text{Equation 2)}$$
$$My = (Max\_G/R + Min\_G/R)/2$$

After that, the expansion center change section 85 shifts the expansion center CES for chroma saturation or the expansion center CEH for hue in the signal ratio space in the vertical direction by the amount Mx of change and in the horizontal direction by the amount My of change.

The fluorescence/reference light amount-calculation section 88 changes the emission ratio of the reference light or obtains the amount of fluorescence and the amount of reference light, which are required for the contents of processing to be performed on the fluorescence and reference image signals, on the basis of the fluorescence and reference image signals and the fluorescence image signals. In this case, the fluorescence/reference light amount-calculation section 88 generates a binarized fluorescence image signal in which a fluorescence component FL and other components of the fluorescence image signal are binarized as shown in FIG. 18. In a case where the fluorescence component FL included in the binarized fluorescence image signal is equal to or lower than the threshold value for fluorescence, the fluorescence/reference light amount-calculation section 88 determines that the fluorescence component FL is not included in the fluorescence image signal and does not calculate the amount of chemical fluorescence. That is, the emission ratio of the reference light is not changed or the contents of processing to be performed on the fluorescence and reference image signals are not changed.

Figure 22:
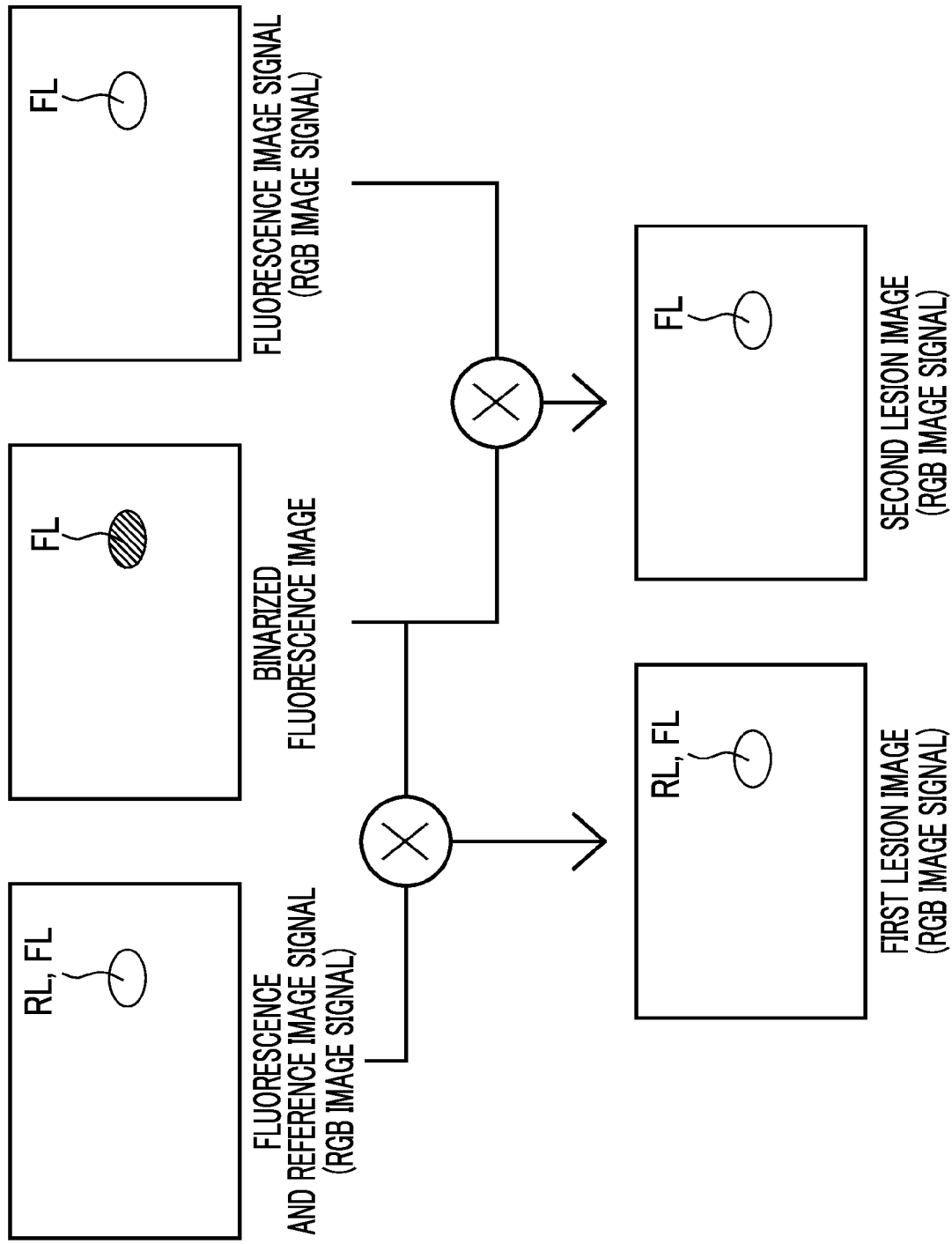
FIG. 22 is a diagram illustrating a method of generating a first lesion image and a second lesion image.

On the other hand, in a case where the fluorescence component FL exceeds the threshold value for fluorescence, the amount of chemical fluorescence is calculated as shown in FIG. 22. The fluorescence/reference light amount-calculation section 88 acquires a first lesion image in which a lesion area including the reference light RL and the fluorescence component FL is displayed by taking a logical product (AND) of the fluorescence and reference image signals and a binarized fluorescence image. In addition to the first lesion image, the fluorescence/reference light amount-calculation section 88 acquires a second lesion image in which a lesion area including the fluorescence component FL is displayed by taking a logical product (AND) of the fluorescence image signals and the binarized fluorescence image.

Figure 23:
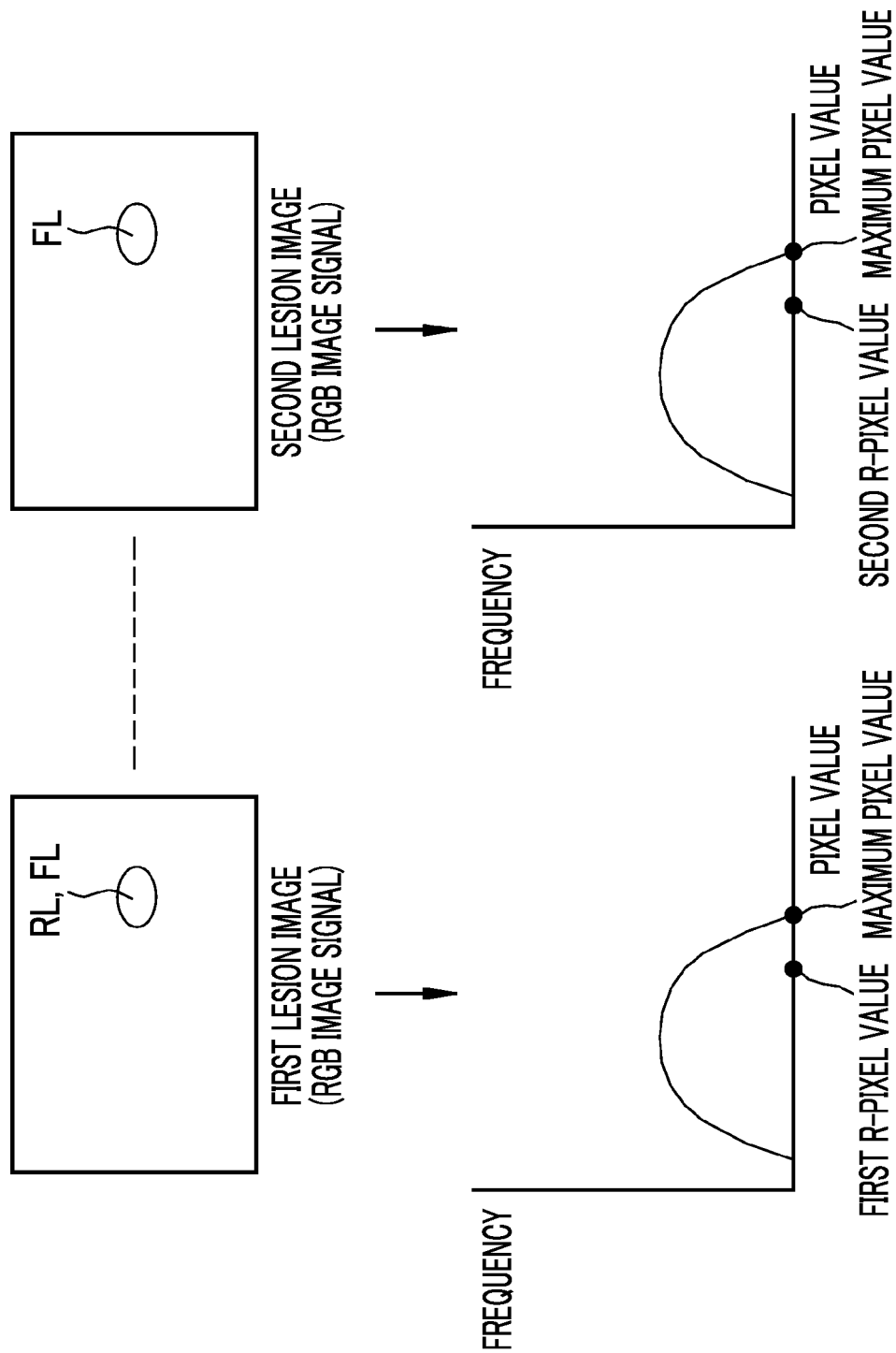
FIG. 23 is a diagram illustrating a method of calculating a first R-pixel value and a second R-pixel value.

Then, as shown in FIG. 23, the fluorescence/reference light amount-calculation section 88 calculates a pixel value, which corresponds to a specific ratio (for example, 80%) of the maximum pixel value included in the frequency distribution (histogram) of the pixel values of the R-image signals of the first lesion image, as a first R-pixel value. The first R-pixel value corresponds to the pixel value of fluorescence and reference light, and a value, which is obtained in a case where the first R-pixel value is divided by an R-gain coefficient for fluorescence observation, corresponds to the amount of fluorescence and reference light. In the same way, the fluorescence/reference light amount-calculation section 88 calculates a pixel value, which corresponds to a specific ratio (for example, 80%) of the maximum pixel value included in the frequency distribution (histogram) of the pixel values of the R-image signals of the second lesion image, as a second R-pixel value. The second R-pixel value corresponds to the pixel value of fluorescence, and a value, which is obtained in a case where the second R-pixel value is divided by the R-gain coefficient for fluorescence observation, corresponds to the amount of fluorescence. Further, the fluorescence/reference light amount-calculation section 88 calculates the pixel value of the reference light by subtracting the second R-pixel value from the first R-pixel value. It is preferable that the first R-pixel value is converted into a linear luminance-signal of which the pixel value changes linearly with respect to the input signal of the image pickup sensor 48. It is preferable that the second R-pixel value is also converted into a linear luminance-signal like the first R-pixel value.

The amount of fluorescence and the amount of reference light, which are obtained by the fluorescence/reference light amount-calculation section 88, are used to change the contents of processing to be performed on the fluorescence and reference image signals, for example, the contents of gain processing or matrix processing and to correct the emission ratio of reference light. A processing change section 91 changes the contents of processing to be performed on the fluorescence and reference image signals on the basis of the amount of fluorescence and the amount of reference light. In a case where, for example, the change of an R-gain coefficient Gn_R for fluorescence observation used for gain processing is to be performed as the change of the contents of the processing, AGn_R is obtained as a changed R-gain coefficient for fluorescence observation by the following equation 3).

$$AGn\_R = \text{pixel value of Max fluorescence}/ \qquad \text{Equation 3)}$$
$$\text{pixel value of fluorescence} \times Gn\_R$$

Here, the pixel value of Max fluorescence means a value that is obtained in a case where the pixel value of the reference light is subtracted from the pixel value of the maximum fluorescence at which the image pickup sensor 48 is saturated.

A reference light amount-correction section 93 corrects the amount of reference light on the basis of the contents of processing that is to be performed on the fluorescence and reference image signals before and after the change. In a case where the change of the R-gain coefficient Gn_R for fluorescence observation is performed as the change of the contents of the processing as described above, the reference light amount-correction section 93 calculates the corrected amount of reference light, which is obtained in a case where the amount of reference light is corrected, by the following equation 4.

Corrected amount of reference light =            Equation 4)

amount of reference light × Gn_R/AGn_R

Then, the light source processor 21 corrects the emission ratio of the reference light on the basis of the corrected amount of reference light. For example, in a case where the emission ratio of light in a fluorescence wavelength range including the components of chemical fluorescence of the reference light, that is, the emission ratio of red light R (light in a fluorescence wavelength range) is to be corrected, the reference light amount-correction section 93 calculates the amount of corrected red light R, which is obtained in a case where the emission ratio of red light R is corrected, by the following equation 5).

Amount of corrected red light $R$ =            Equation 5)

amount of red light × corrected amount of reference light/amount of reference light For example, in a case where chemical fluorescence is detected from an object to be observed so that the amount of chemical fluorescence is equal to or larger than a certain level, the emission ratio of red light R is reduced according to the change of the contents of the processing and the correction of the amount of reference light as the amount of chemical fluorescence is increased. Accordingly, the visibility of chemical fluorescence having the same wavelength range as red light R is improved. On the other hand, in a case where chemical fluorescence is not detected or hardly detected from an object to be observed so that the amount of chemical fluorescence is less than a certain level, the emission ratio of red light R is increased according to the change of the contents of the processing and the correction of the amount of reference light. Accordingly, it is possible to prevent the brightness the red color of an object to be observed from being reduced even though chemical fluorescence is not emitted.

Methods of calculating the amount of fluorescence, the amount of reference light, the corrected R-gain coefficient for fluorescence observation, and the corrected amount of reference light in a case where specific numerical values are used will be described below. As shown in FIG. 24, in a case where the pixel value of fluorescence is "15" and the pixel value of fluorescence and reference light is "165", the pixel value of fluorescence is subtracted from the pixel value of fluorescence and reference light, so that the pixel value of reference light is "150". Further, in a case where an R-gain coefficient for fluorescence observation is set to "1.5", "15", which is the pixel value of fluorescence, is divided by "1.5", which is the R-gain coefficient for fluorescence observation, so that the amount of fluorescence is "10". Furthermore, "150", which is the pixel value of reference light, is divided by "1.5", which is the R-gain coefficient for fluorescence observation, so that the amount of reference light is "100".

Next, the corrected R-gain coefficient AGn_R for fluorescence observation is obtained in a case where the pixel value of Max fluorescence/the pixel value of fluorescence is multiplied by the R-gain coefficient Gn_R for fluorescence observation as shown in Equation 3). "150", which is the pixel value of reference light is subtracted from "230", which is the pixel value of the maximum fluorescence at which the image pickup sensor 48 is saturated, so that the pixel value of Max fluorescence is "80". Accordingly, "80", which is the pixel value of Max fluorescence,/"15", which is the pixel value of fluorescence is multiplied by "1.5", which is the R-gain coefficient Gn_R for fluorescence observation, so that AGn_R is "8".

Next, the amount of reference light is multiplied by Gn_R/AGn_R as shown in Equation 4), so that the corrected amount of reference light is obtained. Specifically, "100", which is the amount of reference light, is multiplied by "1.5", which is Gn_R,/"8", which is AGn_R, so that the corrected amount of reference light is "18.75". With regard to the pixel value of corrected fluorescence, "10", which is the amount of fluorescence substantially constant regardless of the magnitude of the amount of reference light, is multiplied by "8", which is the corrected R-gain coefficient AGn_R for fluorescence observation, so that the pixel value of corrected fluorescence is "80". On the other hand, with regard to the pixel value of corrected reference light, "18.75", which is the corrected amount of reference light, is multiplied by "8", which is the corrected R-gain coefficient for fluorescence observation, so that the pixel value of corrected reference light is "150". With regard to the pixel value of corrected fluorescence and corrected reference light, "80", which is the pixel value of corrected fluorescence, and "150", which is the pixel value of corrected reference light, are added to each other, so that the pixel value of corrected fluorescence and corrected reference light is "230".

Figure 25:
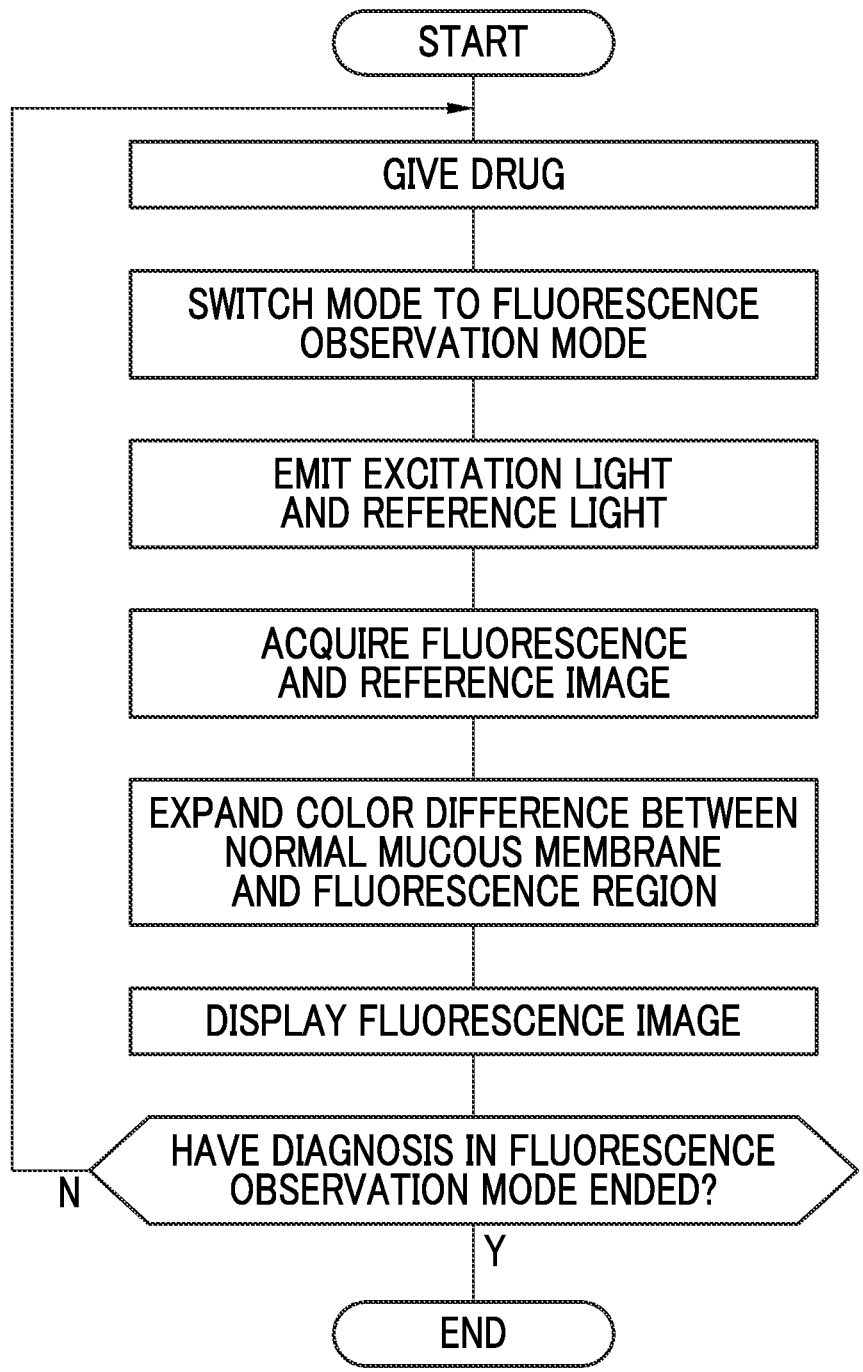
FIG. 25 is a flowchart showing a series of flows of a fluorescence observation mode.

Next, the fluorescence observation mode will be described with reference to a flowchart of FIG. 25. First, a drug, which causes chemical fluorescence to be excited and emitted from an object to be observed, is given to a patient. The mode changeover SW 13a is operated to switch a mode to the fluorescence observation mode. In a case where a mode is switched to the fluorescence observation mode, the light source unit 20 emits excitation light, which causes the drug contained in the object to be observed to be excited to emit chemical fluorescence, and reference light that has a wavelength range from a blue-light wavelength range to a red-light wavelength range. The image pickup sensor 48 picks up the image of the object to be observed, which is illuminated with the excitation light and the reference light, and outputs fluorescence and reference image signals.

The fluorescence and reference image signals, which are output from the image pickup sensor 48, are input to the image signal input unit 53. The signal ratio calculation section 72, which is the color information acquisition section, calculates a B/G ratio and a G/R ratio, which are a plurality of pieces of color information, on the basis of the fluorescence and reference image signals. The color difference expansion section 74 expands a color difference between a normal mucous membrane, which is included in the object to be observed, and a fluorescence region, which includes chemical fluorescence excited and emitted from the drug contained in the object to be observed, in a signal ratio space (feature space) that is formed by the B/G ratio and the G/R ratio. A fluorescence image is obtained on the basis of a B/G ratio and a G/R ratio that are obtained after the expansion of a color difference between the normal mucous membrane and the fluorescence region. The fluorescence image is displayed on the monitor 18. Since the fluorescence image is not a monochrome image including only fluorescence components and includes the components of visible light, which has a wavelength range from a blue-light wavelength range to a red-light wavelength range, the fluorescence image is displayed as a color image. Accordingly, a fluorescence region can be grasped in a situation where the fluorescence image is likely to be visually recognized by a user.

In the above-mentioned embodiment, the B/G ratio and the G/R ratio are obtained from the first RGB image signals by the signal ratio calculation section 72 and the chroma saturation enhancement processing and the hue enhancement processing are performed in the signal ratio space formed by the B/G ratio and the G/R ratio. However, color information different from the B/G ratio and the G/R ratio may be obtained and the chroma saturation enhancement processing and the hue enhancement processing may be performed in a feature space formed by the color information.

Figure 26:
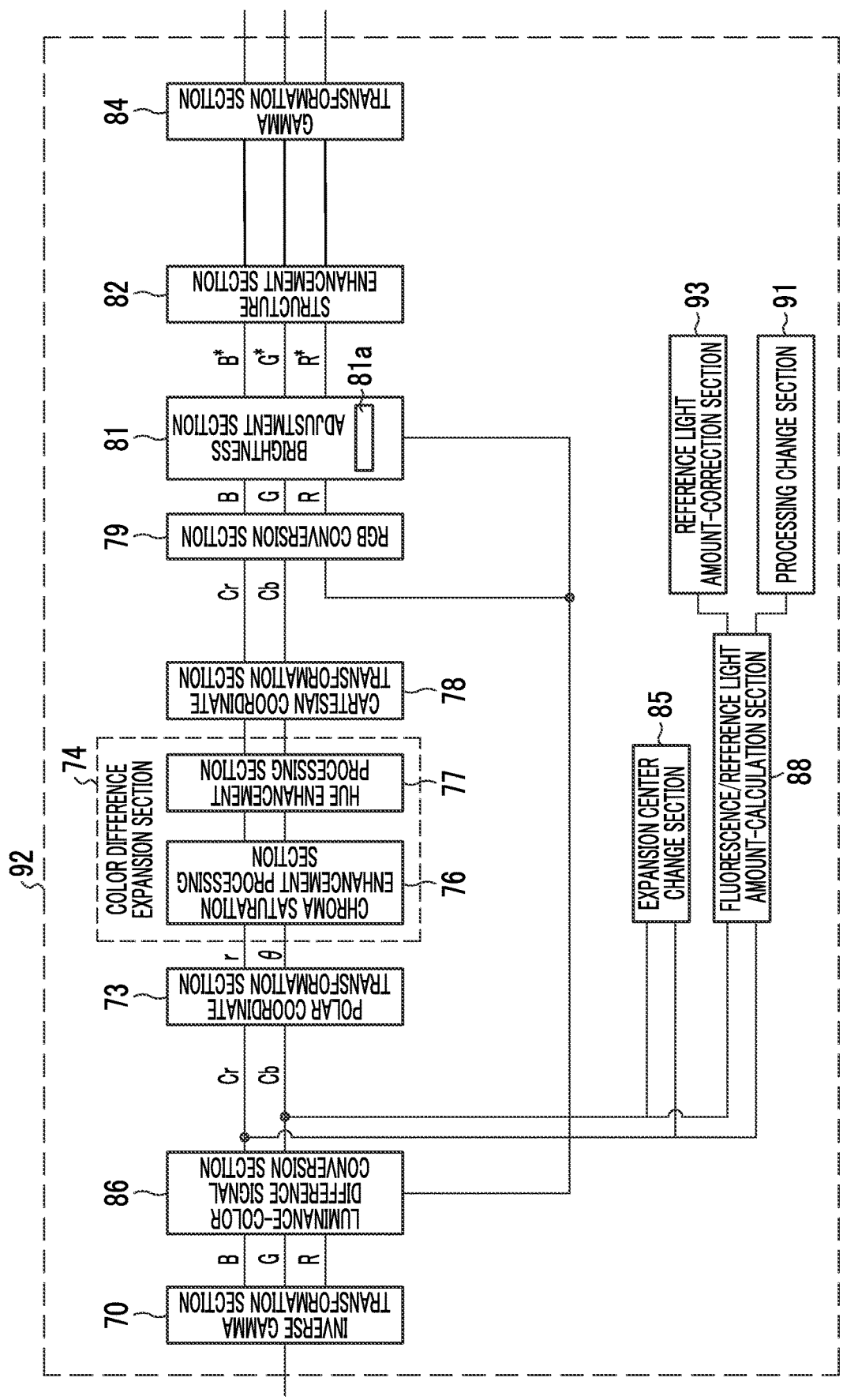
FIG. 26 is a block diagram showing the functions of a fluorescence image processing unit that is used in a case where a feature space is a CrCb space.

For example, color difference signals Cr and Cb may be obtained as the color information, and the chroma saturation enhancement processing and the hue enhancement processing may be performed in a feature space formed by the color difference signals Cr and Cb. In this case, a fluorescence image processing unit 92 shown in FIG. 26 is used. Unlike the fluorescence image processing unit 64, the fluorescence image processing unit 92 does not comprise the Log transformation section 71, the signal ratio calculation section 72, and the inverse Log transformation section 83. The fluorescence image processing unit 92 comprises a luminance-color difference signal conversion section 86 instead. Other components of the fluorescence image processing unit 92 are the same as those of the fluorescence image processing unit 64.

The luminance-color difference signal conversion section 86 (corresponding to "color information acquisition section" of the present invention) converts the first RGB image signals into a luminance signal Y and color difference signals Cr and Cb. A well-known conversion equation is used for the conversion of the first RGB image signals into the color difference signals Cr and Cb. The color difference signals Cr and Cb are transmitted to the polar coordinate transformation section 73. The luminance signal Y is transmitted to the RGB conversion section 79 and the brightness adjustment section 81. The RGB conversion section 79 converts the color difference signals Cr and Cb, which have passed through the Cartesian coordinate transformation section 78, and the luminance signal Y into second RGB image signals. The brightness adjustment section 81 uses the luminance signal Y as the first brightness information Yin, and uses the second brightness information, which is obtained by the second brightness information-calculation section 81b, as the second brightness information Yout to adjust the pixel values of the second RGB image signals. A method of calculating the second brightness information Yout and a method of adjusting the pixel values of the second RGB image signals are the same as those in the case of the fluorescence image processing unit 64.

Figure 27:
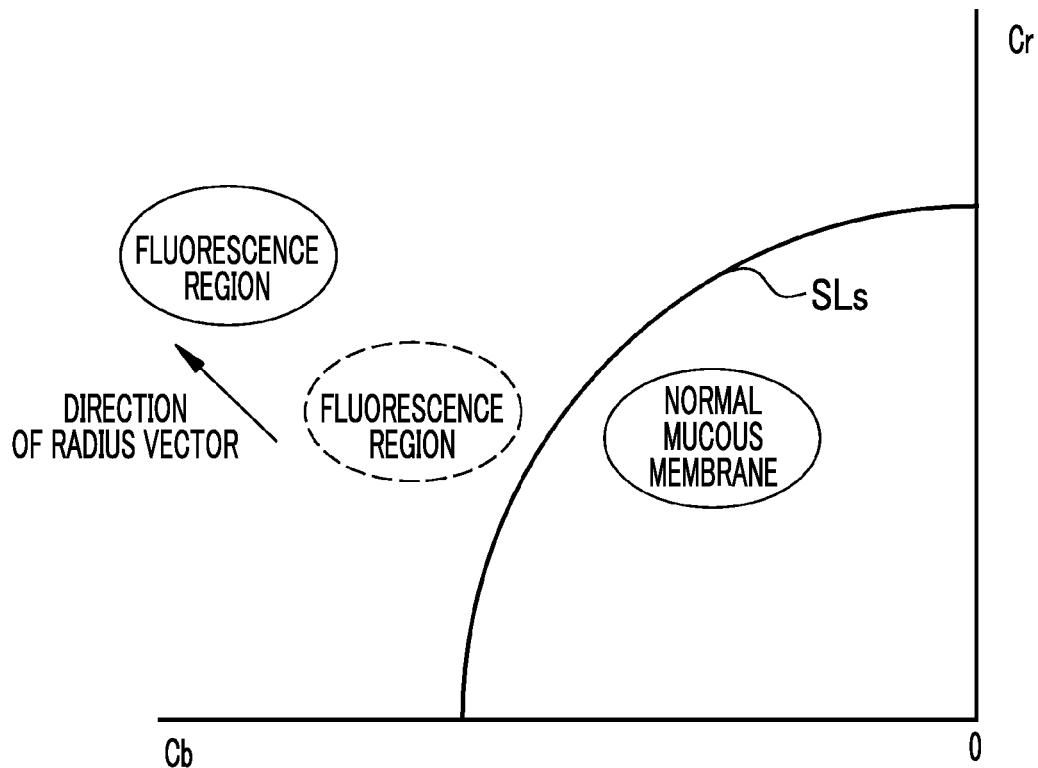
FIG. 27 is a diagram illustrating a positional relationship between fluorescence regions before and after chroma saturation enhancement processing in the CrCb space.
Figure 28:
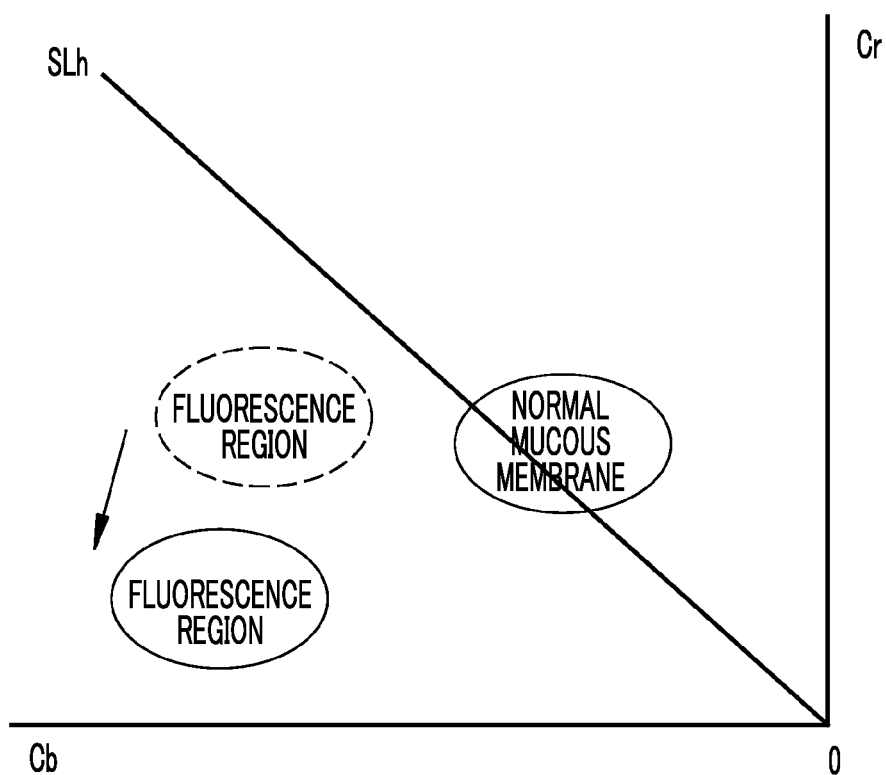
FIG. 28 is a diagram illustrating a positional relationship between fluorescence regions before and after hue enhancement processing in the CrCb space.

Further, as in the case of the signal ratio space, a radius vector r and an angle θ in a CrCb space that is a feature space consisting of the color difference signals Cr and Cb are changed to perform the chroma saturation enhancement processing or the hue enhancement processing. Accordingly, in a case where the chroma saturation enhancement processing is performed in the CrCb space, a fluorescence region (solid line) subjected to the chroma saturation enhancement processing is moved to be farther from an expansion center line SLs for chroma saturation than a fluorescence region (dotted line) not yet subjected to the chroma saturation enhancement processing as shown in FIG. 27. Further, in a case where the hue enhancement processing, a fluorescence region (solid line) subjected to the hue enhancement processing is moved to be farther from an expansion center line SLh for hue than a fluorescence region (dotted line) not yet subjected to the hue enhancement processing as shown in FIG. 28.

Figure 29:
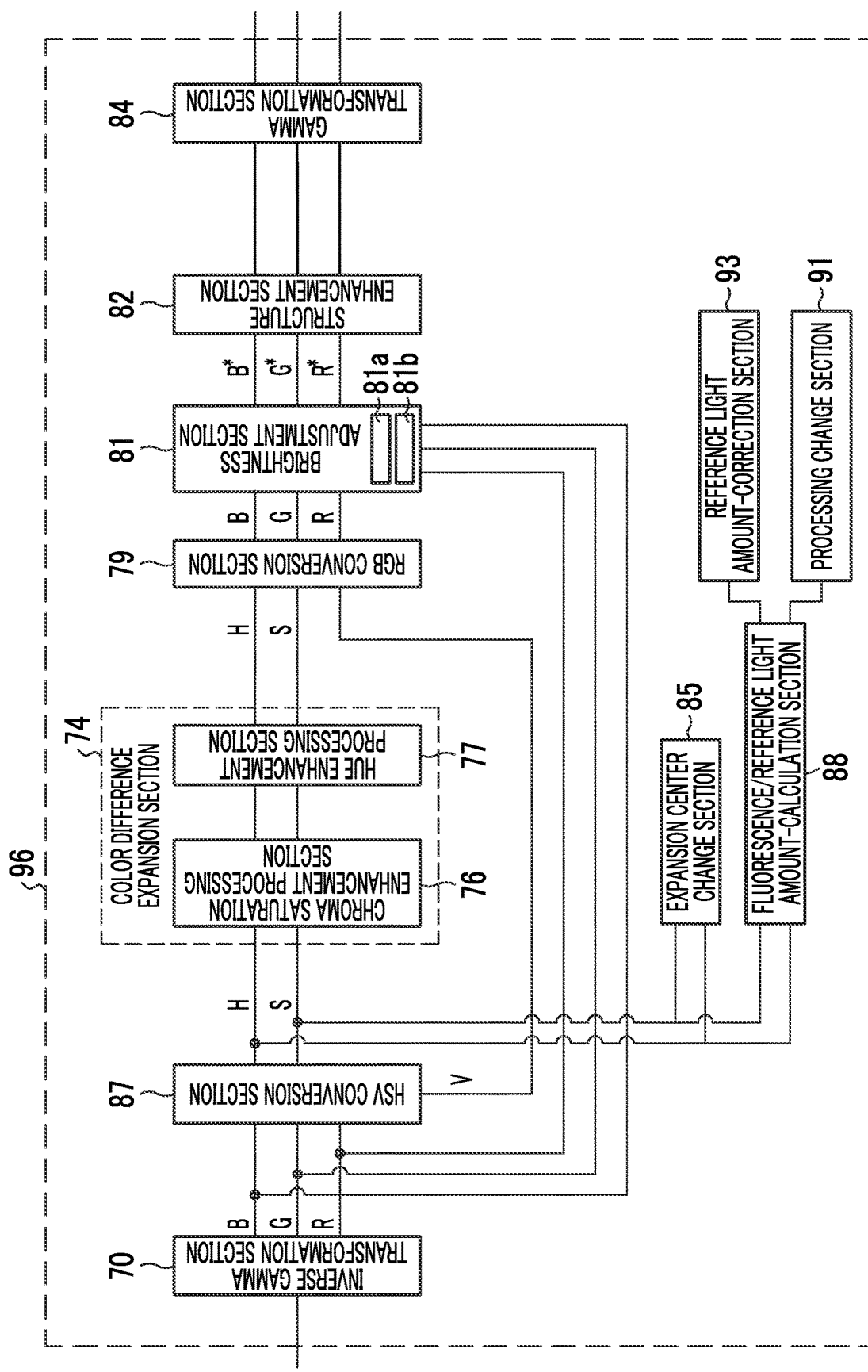
FIG. 29 is a block diagram showing the functions of a fluorescence image processing unit that is used in a case where a feature space is a HS space.

Further, hue H(Hue) and chroma saturation S(Saturation) may be obtained as the color information, and the chroma saturation enhancement processing and the hue enhancement processing may be performed in a HS space formed by the hue H and the chroma saturation S. In a case where the hue H and the chroma saturation S are used, a fluorescence image processing unit 96 shown in FIG. 29 is used. Unlike the fluorescence image processing unit 64, the fluorescence image processing unit 96 does not comprise the Log transformation section 71, the signal ratio calculation section 72, the polar coordinate transformation section 73, the Cartesian coordinate transformation section 78, and the inverse Log transformation section 83. The fluorescence image processing unit 96 comprises a HSV conversion section 87 instead. Other components of the fluorescence image processing unit 96 are the same as those of the fluorescence image processing unit 64.

The HSV conversion section 87 (corresponding to "color information acquisition section" of the present invention) converts the first RGB image signals into hue H, chroma saturation S, and value V. A well-known conversion equation is used for the conversion of the first RGB image signals into the hue H, the chroma saturation S, and the value V. The hue H and the chroma saturation S are transmitted to a translation section 90. The value V is transmitted to the RGB conversion section 79. The RGB conversion section 79 converts the hue H and the chroma saturation S, which have passed through the translation section 90, and the value V into second RGB image signals. The brightness adjustment section 81 uses the first brightness information Yin, which is obtained by the first brightness information-calculation section, and the second brightness information Yout, which is obtained by the second brightness information-calculation section 81b, to adjust the pixel values of the second RGB image signals. Methods of calculating the first brightness information Yin and the second brightness information Yout and a method of adjusting the pixel values of the second RGB image signals are the same as those in the case of the fluorescence image processing unit 64.

Figure 30:
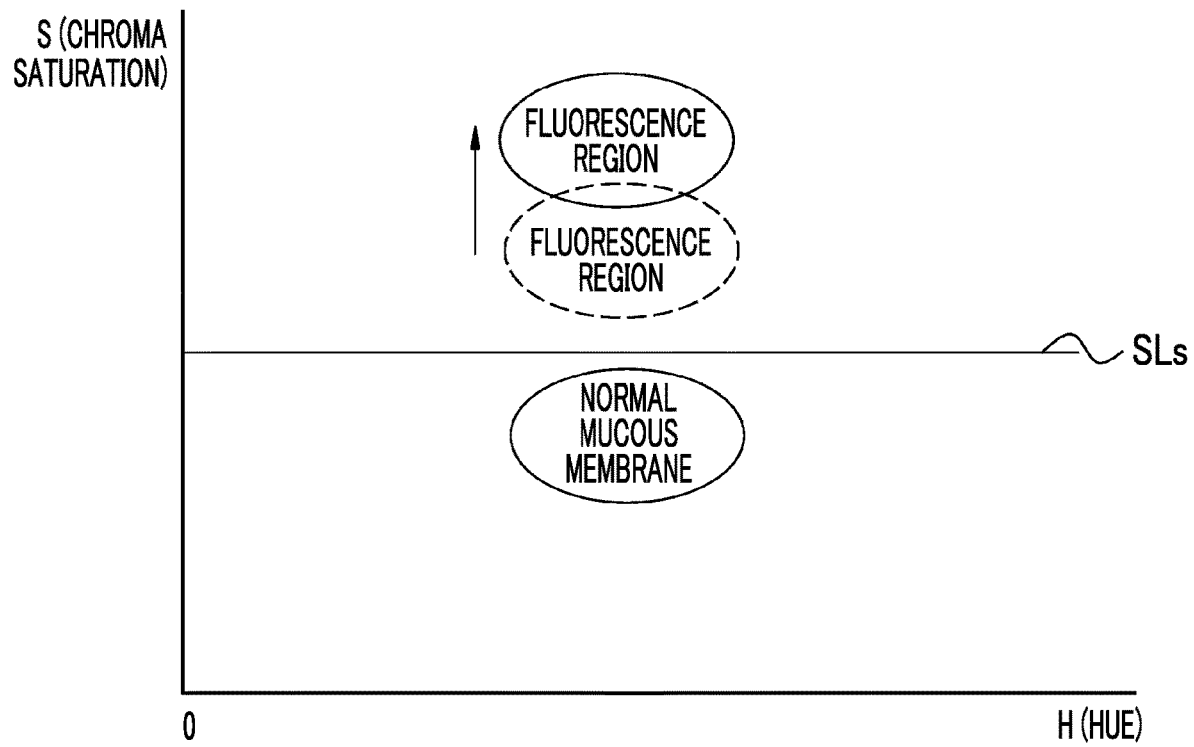
FIG. 30 is a diagram illustrating a positional relationship between fluorescence regions before and after chroma saturation enhancement processing in the HS space.
Figure 31:
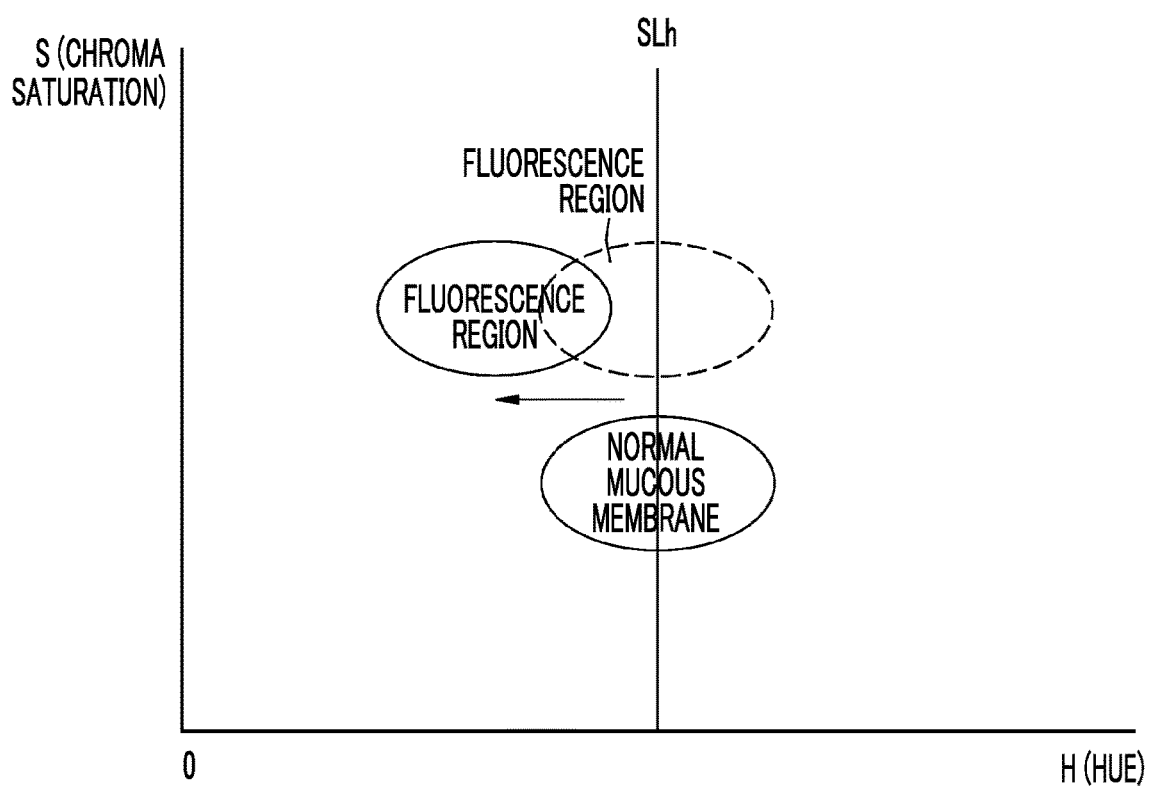
FIG. 31 is a diagram illustrating a positional relationship between fluorescence regions before and after hue enhancement processing in the HS space.

The chroma saturation enhancement processing and the hue enhancement processing in a HS space formed by the hue H and the chroma saturation S do not expand or compress the radius vector r and the angle θ as in the signal ratio space and the CrCb space, and is performed as processing for translating each pixel. In a case where chroma saturation enhancement processing is performed in the HS space rather than normal chroma saturation enhancement processing and normal hue enhancement processing to be performed in the HS space, a fluorescence region (solid line) subjected to the chroma saturation enhancement processing is moved to be farther from an expansion center line SLs for chroma saturation than a fluorescence region (dotted line) not yet subjected to the chroma saturation enhancement processing as shown in FIG. 30. Further, in a case where hue enhancement processing is performed, a fluorescence region (solid line) subjected to the hue enhancement processing is moved to be farther from an expansion center line SLh for hue than a fluorescence region (dotted line) not yet subjected to the hue enhancement processing as shown in FIG. 31.

Second Embodiment

In a second embodiment, an object to be observed is illuminated using a laser light source and a phosphor instead of the four color LEDs 20a to 20d described in the first embodiment. Others are the same as those of the first embodiment.

Figure 32:
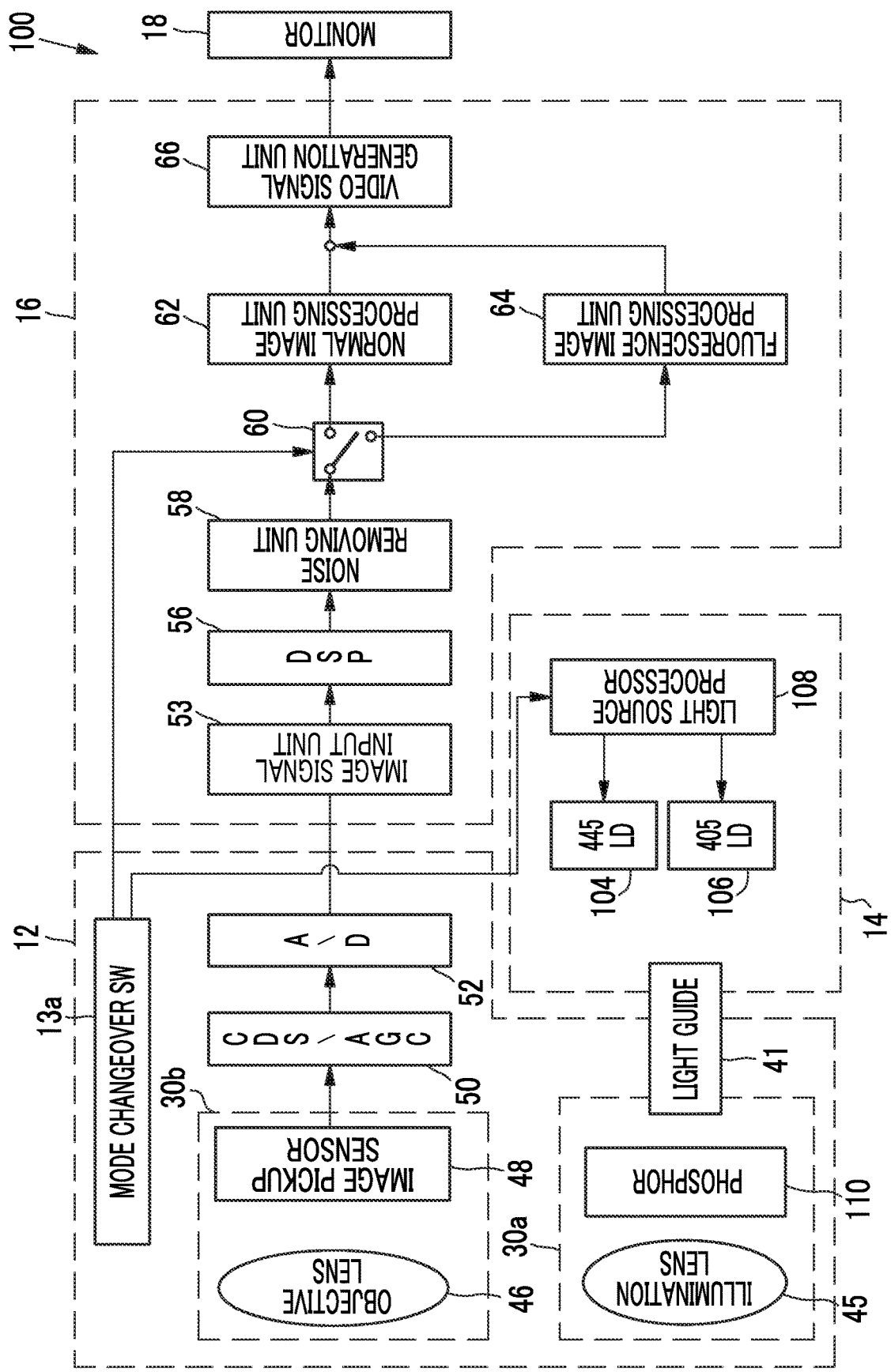
FIG. 32 is a block diagram showing the functions of an endoscope system according to a second embodiment.

As shown in FIG. 32, in an endoscope system 100 according to a second embodiment, a light source device 14 is provided with a blue laser light source (written in FIG. 32 as "445LD") 104 emitting blue laser light of which the central wavelength is in the range of 445±10 nm and a blue-violet laser light source (written in FIG. 32 as "405LD") 106 emitting blue-violet laser light of which the central wavelength is in the range of 405±10 nm, instead of the four color LEDs 20a to 20d. Since the emission of light from semiconductor light-emitting elements of the respective light sources 104 and 106 is individually controlled by a light source processor 108, a ratio of the amount of light emitted from the blue laser light source 104 to the amount of light emitted from the blue-violet laser light source 106 can be freely changed.

The light source processor 108 drives the blue laser light source 104 in the case of the normal observation mode. On the other hand, in the case of the fluorescence observation mode, the light source processor 108 drives both the blue laser light source 104 and the blue-violet laser light source 106 at the reference frame and drives only the blue-violet laser light source 106 at the fluorescence frame. Laser light emitted from each of the above-mentioned light sources 104 and 106 is incident on the light guide 41 through optical members (all of the optical members are not shown), such as a condenser lens, optical fibers, or a multiplexer.

It is preferable that the half-width of blue laser light or blue-violet laser light is set to about ±10 nm. Further, broad area-type InGaN-based laser diodes can be used as the blue laser light source 104 and the blue-violet laser light source 106, and InGaNAs-based laser diodes or GaNAs-based laser diodes can also be used. Furthermore, a light emitter, such as a light emitting diode, may be used as the light source.

The illumination optical system 30a is provided with a phosphor 110 on which blue laser light or blue-violet laser light transmitted from the light guide 41 is to be incident in addition to the illumination lens 45. In a case where the phosphor 110 is irradiated with blue laser light, fluorescence for a phosphor is emitted from the phosphor 110. Further, a part of blue laser light is transmitted through the phosphor 110 as it is. Blue-violet laser light is transmitted through the phosphor 110 without exciting the phosphor 110. The inside of a sample is irradiated with light, which is emitted from the phosphor 110, through the illumination lens 45.

Figure 33:
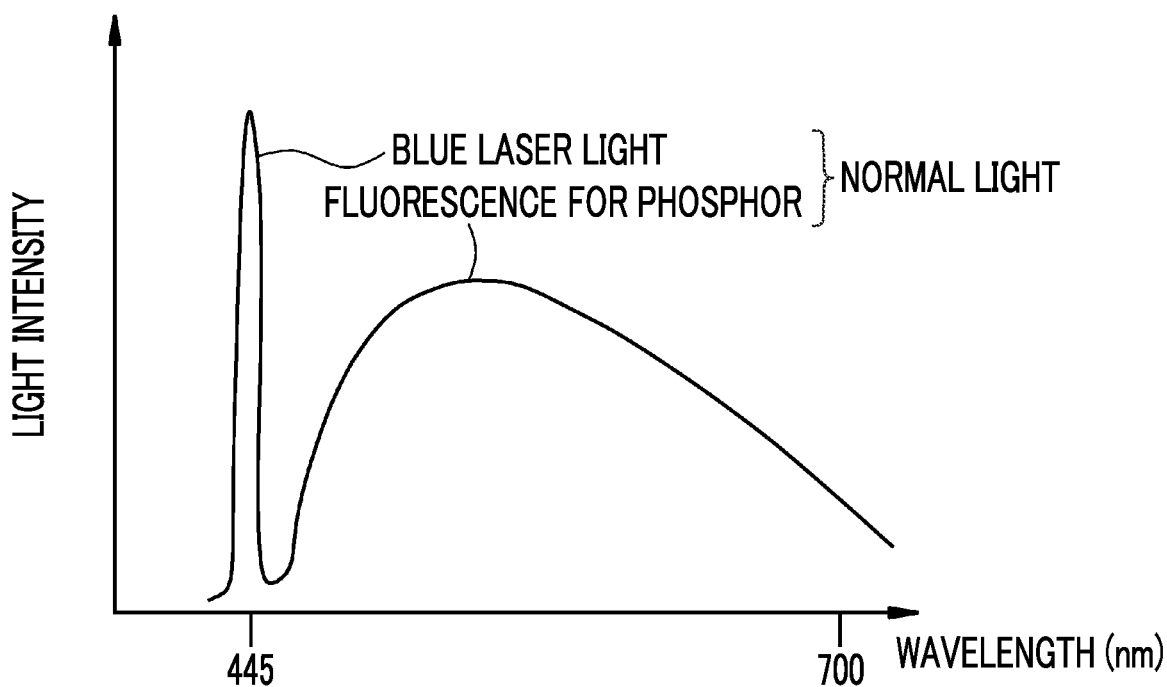
FIG. 33 is a graph showing the emission spectrum of normal light.
Figure 34:
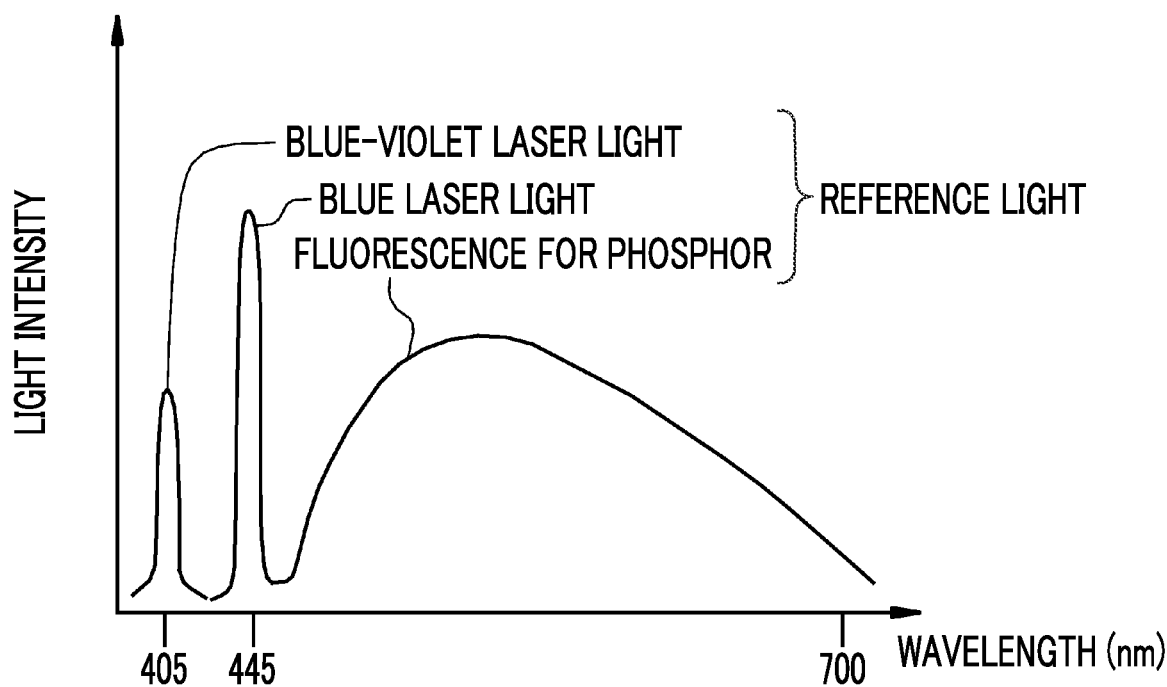
FIG. 34 is a graph showing the emission spectrum of reference light.
Figure 35:
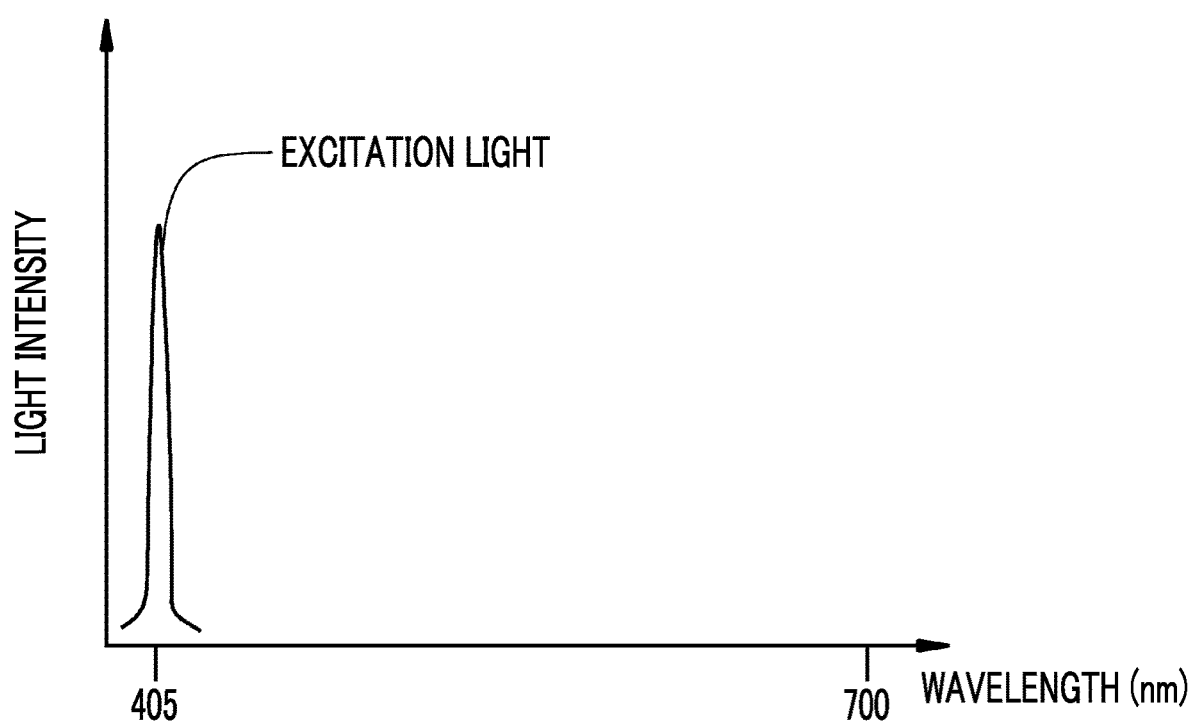
FIG. 35 is a graph showing the emission spectrum of excitation light.

Here, since blue laser light is mainly incident on the phosphor 110 in the normal observation mode, an object to be observed is irradiated with normal light shown in FIG. 33 in which blue laser light and fluorescence for a phosphor excited and emitted from the phosphor 110 due to blue laser light are multiplexed. On the other hand, since both blue-violet laser light and blue laser light are incident on the phosphor 110 at the reference frame in the fluorescence observation mode, the inside of the sample is irradiated with reference light shown in FIG. 34 in which excitation light, which is blue-violet laser light, blue laser light, and fluorescence for a phosphor excited and emitted from the phosphor 110 due to blue laser light are multiplexed. Further, since only blue-violet laser light is incident on the phosphor 110 at the fluorescence frame, the inside of the sample is irradiated with excitation light shown in FIG. 35 that is blue-violet laser light transmitted through the phosphor as it is.

It is preferable that a phosphor including plural kinds of phosphors absorbing a part of blue laser light and excited by green to yellow light to emit light (for example, YAG-based phosphors or phosphors, such as BAM ($BaMgAl_{10}O_{17}$)) is used as the phosphor 110. In a case where the semiconductor light-emitting elements are used as the excitation light source of the phosphor 110 as in this example of configuration, high-intensity white light is obtained with high luminous efficacy and not only the intensity of white light can be easily adjusted but also a change in the color temperature and chromaticity of white light can be suppressed to be small.

Third Embodiment

In a third embodiment, an object to be observed is illuminated using a broadband light source, such as a xenon lamp, and a rotary filter instead of the four color LEDs 20a to 20d described in the first embodiment. Further, the image of the object to be observed is picked up by a monochrome image pickup sensor instead of the color image pickup sensor 48. Others are the same as those of the first embodiment.

Figure 36:
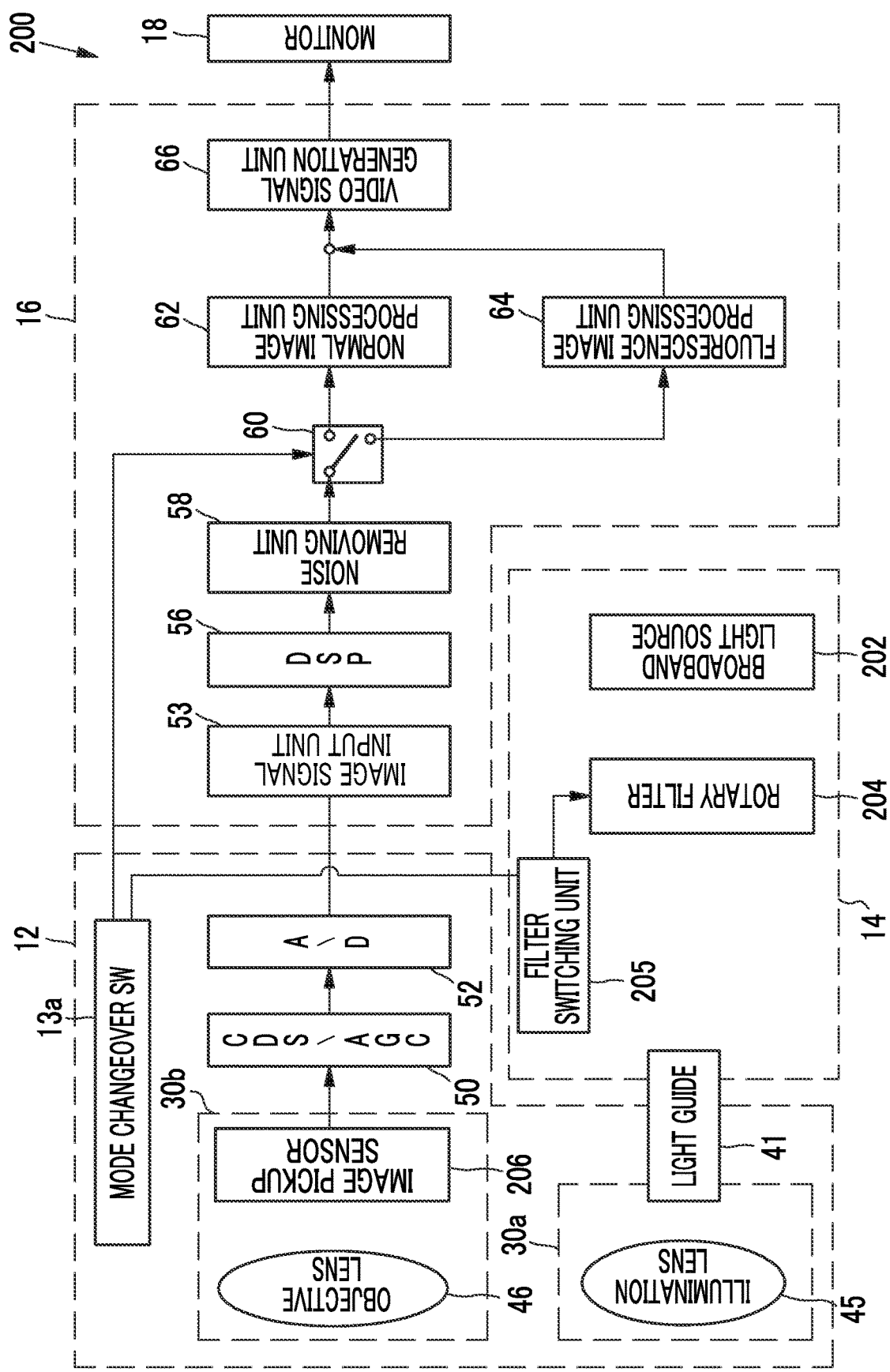
FIG. 36 is a block diagram showing the functions of an endoscope system according to a third embodiment.

As shown in FIG. 36, in an endoscope system 200 according to a third embodiment, a light source device 14 is provided with a broadband light source 202, a rotary filter 204, and a filter switching unit 205 instead of the four color LEDs 20a to 20d. Further, an image pickup optical system 30b is provided with a monochrome image pickup sensor 206, which is not provided with a color filter, instead of the color image pickup sensor 48.

The broadband light source 202 is a xenon lamp, a white LED, or the like, and emits white light of which the wavelength range reaches the wavelength range of red light from the wavelength range of blue light. The rotary filter 204 comprises a filter 208 for a normal observation mode provided on the inside and a filter 209 for a fluorescence observation mode provided on the outside (see FIG. 37). The filter switching unit 205 is to move the rotary filter 204 in a radial direction, inserts the filter 208 for a normal observation mode of the rotary filter 204 into the optical path of white light in a case where a mode is set to the normal observation mode by the mode changeover SW 13a, and inserts the filter 209 for a fluorescence observation mode of the rotary filter 204 into the optical path of white light in a case where a mode is set to the fluorescence observation mode.

Figure 37:
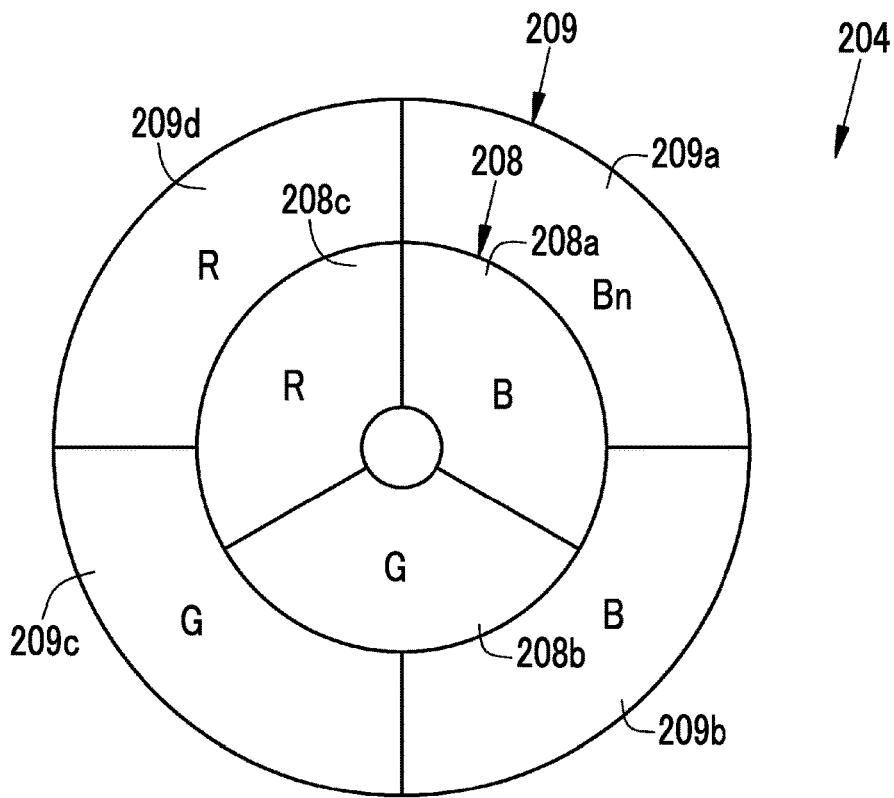
FIG. 37 is a plan view of a rotary filter.

As shown in FIG. 37, the filter 208 for a normal observation mode is provided with a B-filter 208a, a G-filter 208b, and an R-filter 208c that are arranged in a circumferential direction. The B-filter 208a transmits blue light of white light, the G-filter 208b transmits green light of white light, and the R-filter 208c transmits red light of white light. Accordingly, in a case where the rotary filter 204 is rotated in the normal observation mode, the object to be observed is alternately irradiated with blue light, green light, and red light.

The filter 209 for a fluorescence observation mode is provided with a Bn-filter 209a, a B-filter 209b, a G-filter 209c, and an R-filter 209d that are arranged in the circumferential direction. The Bn-filter 209a transmits narrow-band blue light, which has a specific wavelength, of white light, the B-filter 209b transmits blue light of white light, the G-filter 209c transmits green light of white light, and the R-filter 209d transmits red light of white light. Accordingly, in a case where the rotary filter 204 is rotated in the fluorescence observation mode, the object to be observed is alternately irradiated with narrow-band blue light, blue light, green light, and red light. Image signals based on narrow-band blue light are combined with image signals based on blue light, and are used as the B-image signals of fluorescence and reference image signals. Image signals based on green light are used as the G-image signals of fluorescence and reference image signals, and image signals based on red light are used as the R-image signals of fluorescence and reference image signals. Image signals based on narrow-band blue light are used as fluorescence image signals.

In the endoscope system 200, in the normal observation mode, the image of the inside of the sample is picked up by the monochrome image pickup sensor 206 whenever the object to be observed is irradiated with blue light, green light, and red light. Accordingly, image signals corresponding to three colors of R, G, and B are obtained. Then, a normal image is generated by the same method as the first embodiment on the basis of the image signals corresponding to R, G, and B.

On the other hand, in the fluorescence observation mode, the image of the inside of the sample is picked up by the monochrome image pickup sensor 206 whenever the object to be observed is irradiated with narrow-band blue light, green light, and red light. Accordingly, Bn-image signals, G-image signals, and R-image signals are obtained. A special image is generated on the basis of the Bn-image signals, the G-image signals, and the R-image signals. The Bn-image signals are used instead of the B-image signals to generate the special image. Except for that, the special image is generated by the same method as the first embodiment.

Figure 38:
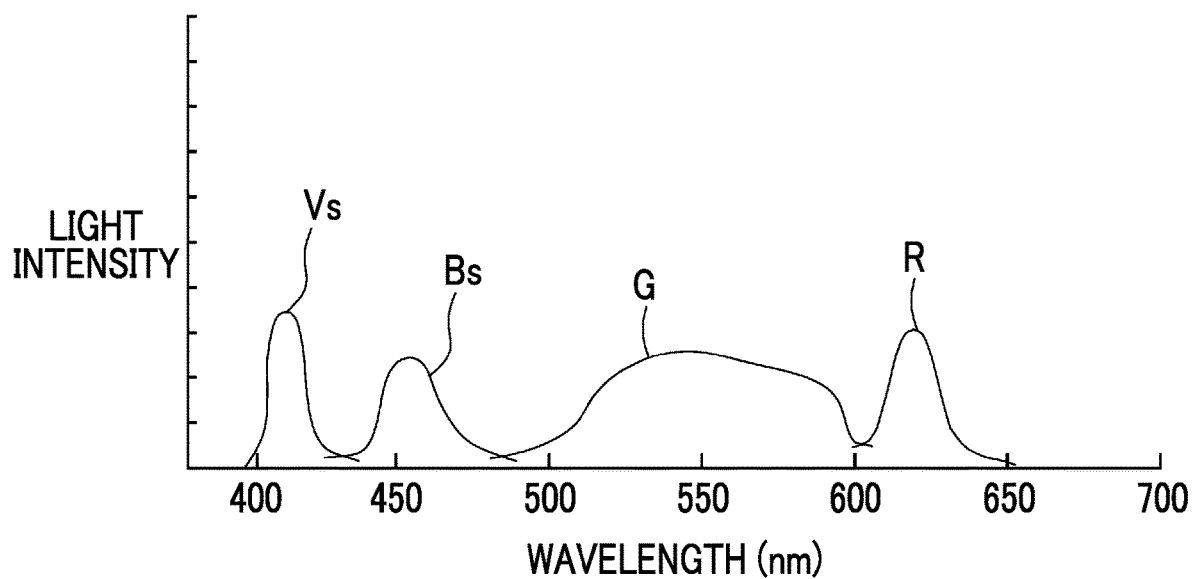
FIG. 38 is a graph showing the emission spectra of violet light V, blue light B, green light G, and red light R different from FIG. 3.

Four types of color light having the emission spectra shown in FIG. 3 are used in the embodiment, but the emission spectra are not limited thereto. For example, as shown in FIG. 38, green light G and red light R have the same spectra as those shown in FIG. 3 but light of which the central wavelength is in the range of 410 to 420 nm and the wavelength range is slightly closer to a long wavelength side than that of violet light V shown in FIG. 3 may be used as violet light Vs. Further, light of which the central wavelength is in the range of 445 to 460 nm and the wavelength range is slightly closer to a short wavelength side than that of blue light B shown in FIG. 3 may be used as blue light Bs.

Figure 39:
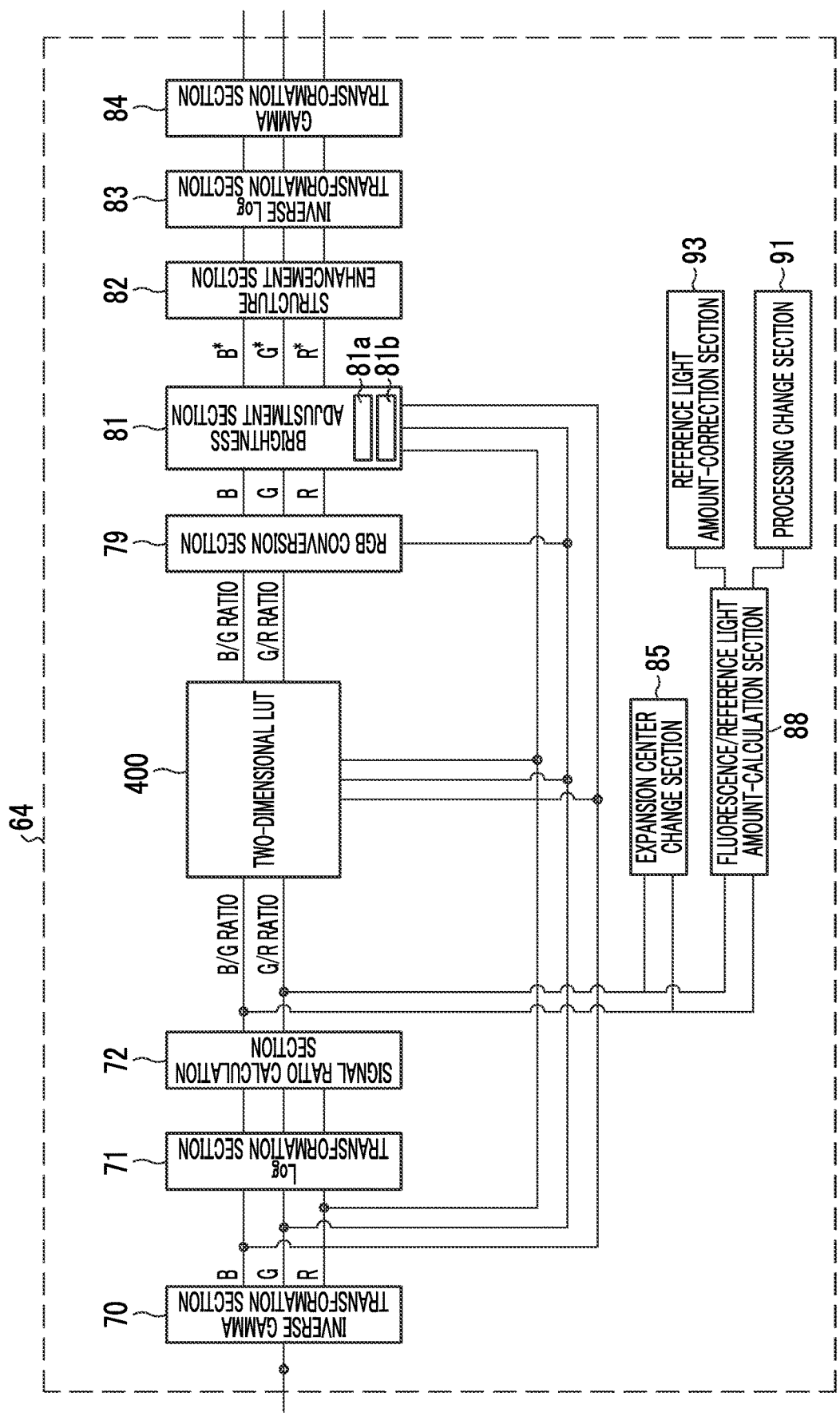
FIG. 39 is a block diagram showing the functions of a fluorescence image processing unit that is used in a case where a two-dimensional LUT is used.

In the first embodiment, a B/G ratio and a G/R ratio have been transformed into a radius vector r and an argument θ by polar coordinate transformation, the chroma saturation enhancement processing and the hue enhancement processing for expanding or compressing an angle on the basis of the radius vector r and the argument θ having been transformed have been performed, and the radius vector r and the argument θ then have been returned to a B/G ratio and a G/R ratio again. However, as shown in FIG. 39, a B/G ratio and a G/R ratio may be directly converted into a B/G ratio and a G/R ratio, which have been subjected to first or second processing, using a two-dimensional look up table (LUT) 400 without polar coordinate transformation or the like from a B/G ratio and a G/R ratio.

A B/G ratio and a G/R ratio and a B/G ratio and a G/R ratio having been subjected to chroma saturation enhancement processing and hue enhancement processing, which are obtained from the chroma saturation enhancement processing and the hue enhancement processing based on the B/G ratio and the G/R ratio, are stored in the two-dimensional LUT 400 in association with each other. Here, in a case where a mode is set to a normal chroma saturation enhancement mode, a correspondence relationship between a B/G ratio and a G/R ratio and a B/G ratio and a G/R ratio having been subjected to normal chroma saturation enhancement processing and normal hue enhancement processing is used. In a case where a mode is set to a specific chroma saturation enhancement mode, a correspondence relationship between a B/G ratio and a G/R ratio and a B/G ratio and a G/R ratio having been subjected to normal chroma saturation enhancement processing and specific hue enhancement processing is used. Further, first RGB image signals output from the inverse gamma transformation section 70 are input to the two-dimensional LUT 400 and the RGB conversion section 79.

The hardware structures of the processing units, which are included in the processor device 16 in the embodiments, such as the image signal input unit 53, the noise removing unit 58, the signal switching unit 60, the normal image processing unit 62, the fluorescence image processing unit 64, the fluorescence image processing unit 92, the fluorescence image processing unit 96, the video signal generation unit 66, the inverse gamma transformation section 70, the Log transformation section 71, the signal ratio calculation section 72, the polar coordinate transformation section 73, the color difference expansion section 74, the chroma saturation enhancement processing section 76, the hue enhancement processing section 77, the Cartesian coordinate transformation section 78, the RGB conversion section 79, the brightness adjustment section 81, the structure enhancement section 82, the inverse Log transformation section 83, the gamma transformation section 84, the expansion center change section 85, the fluorescence/reference light amount-calculation section 88, the reference light amount-correction section 93, the processing change section 91, the luminance-color difference signal conversion section 86, and the HSV conversion section 87, are various processors to be described below. The various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit that is a processor having circuit configuration designed exclusively to perform various types of processing; and the like.

One processing unit may be formed of one of these various processors, or may be formed of a combination of two or more same type or different types of processors (for example, a plurality of FPGAs, or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by a system-on-chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined. Further, the hardware structure of a storage unit is a storage device, such as a hard disc drive (HDD) or a solid state drive (SSD).

EXPLANATION OF REFERENCES

10: endoscope system
12: endoscope
12a: insertion part
12b: operation part
12c: bendable part
12d: distal end part
12e: angle knob
13a: mode changeover SW
14: light source device
16: processor device
18: monitor
19: user interface
20: light source unit
20a: V-LED
20b: B-LED
20c: G-LED
20d: R-LED
21: light source processor
23: optical path-combination unit
30a: illumination optical system
30b: image pickup optical system
41: light guide
45: illumination lens
46: objective lens
48: image pickup sensor
50: CDS/AGC circuit
52: A/D converter
53: image signal input unit
56: DSP
58: noise removing unit
60: signal switching unit
62: normal image processing unit
64: fluorescence image processing unit
66: video signal generation unit
70: inverse gamma transformation section
71: Log transformation section
72: signal ratio calculation section
73: polar coordinate transformation section
74: color difference expansion section
76: chroma saturation enhancement processing section
77: hue enhancement processing section
78: Cartesian coordinate transformation section
79: RGB conversion section
81: brightness adjustment section
81a: first brightness information-calculation section
81b: second brightness information-calculation section
82: structure enhancement section
83: inverse Log transformation section
84: gamma transformation section
85: expansion center change section
86: luminance-color difference signal conversion section
87: HSV conversion section
88: fluorescence/reference light amount-calculation section
91: processing change section
92: fluorescence image processing unit
93: reference light amount-correction section
96: fluorescence image processing unit
100: endoscope system
104: blue laser light source
106: blue-violet laser light source
108: light source processor
110: phosphor
200: endoscope system
202: broadband light source
204: rotary filter
205: filter switching unit
206: image pickup sensor
208: filter for normal observation mode
208a: B-filter
208b: G-filter
208c: R-filter
209: filter for fluorescence observation mode
209a: Bn-filter
209b: B-filter
209c: G-filter
209d: R-filter
400: two-dimensional LUT
SLs: expansion center line for chroma saturation
SLh: expansion center line for hue
CES: expansion center for chroma saturation
CEH: expansion center for hue

What is claimed is:

1. An endoscope system comprising:
a light source that emits excitation light, which causes a drug contained in an object to be observed to be excited to emit chemical fluorescence, and reference light which has at least a wavelength range from a blue-light wavelength range to a red-light wavelength range; and
an image control processor configured to:
receive fluorescence and reference image signals, which are obtained from image pickup of the object to be observed illuminated with the excitation light and the reference light;
acquire a plurality of pieces of color information from the fluorescence and reference image signals; and
expand a color difference between a normal mucous membrane and a fluorescence region, which includes the chemical fluorescence, in a feature space formed by the plurality of pieces of color information, by expanding a chroma saturation difference and a hue difference between the normal mucous membrane and the fluorescence region.

2. The endoscope system according to claim 1,
wherein the color difference between the normal mucous membrane and the fluorescence region is increased by being expanded around an expansion center determined in the feature space.

3. The endoscope system according to claim 2,
wherein the image control processor is further configured to change the expansion center on the basis of the fluorescence and reference image signals and fluorescence image signals that are obtained from image pickup of the object to be observed illuminated with only the excitation light.

4. The endoscope system according to claim 3,
wherein the image control processor is further configured to change the expansion center on the basis of reference image signals that are obtained from a difference between the fluorescence and reference image signals and the fluorescence image signals.

5. The endoscope system according to claim 3,
wherein the image control processor is further configured to calculate an amount of change of the expansion center on the basis of components of fluorescence and reference light included in the fluorescence and reference image signals and components of fluorescence included in the fluorescence image signals.

6. The endoscope system according to claim 3,
wherein the image control processor is further configured to:
generate a first lesion image in which a lesion area including components of the fluorescence and reference light is displayed and a lesion-excluding image in which portions other than the lesion area including the components of the fluorescence and the reference light are displayed, from the fluorescence and reference image signals and the fluorescence image signals; and
calculate an amount of change of the expansion center on the basis of the first lesion image and the lesion-excluding image.

7. The endoscope system according to claim 1, further comprising:
a light source processor configured to switch a reference frame where the excitation light and the reference light are emitted and a fluorescence frame where only the excitation light is emitted at a specific number of frames.

8. The endoscope system according to claim 7,
wherein the image control processor is further configured to calculate an amount of the fluorescence and an amount of the reference light on the basis of the fluorescence and reference image signals and fluorescence image signals obtained at the fluorescence frame.

9. The endoscope system according to claim 8,
wherein the image control processor is further configured to:
acquire a first lesion image in which a lesion area including components of the fluorescence and reference light is displayed and a second lesion image in which a lesion area including components of the fluorescence is displayed, on the basis of the fluorescence and reference image signals and the fluorescence image signals; and
calculate an amount of the fluorescence and an amount of the reference light on the basis of the first lesion image and the second lesion image.

10. The endoscope system according to claim 8,
wherein the image control processor is further configured to change contents of processing to be performed on the fluorescence and reference image signals on the basis of the amount of the fluorescence and the amount of the reference light.

11. The endoscope system according to claim 10,
wherein the contents of the processing are gain processing or matrix processing.

12. The endoscope system according to claim 10,
wherein the image control processor is further configured to correct the amount of the reference light on the basis of the contents of the processing before and after the change.

13. A method of operating an endoscope system, the method comprising:
a step of emitting excitation light, which causes a drug contained in an object to be observed to be excited to emit chemical fluorescence, and reference light which has a wavelength range from a blue-light wavelength range to a red-light wavelength range;
a step of inputting fluorescence and reference image signals that are obtained from image pickup of the object to be observed illuminated with the excitation light and the reference light;
a step of acquiring a plurality of pieces of color information from the fluorescence and reference image signals; and
a step of expanding a color difference between a normal mucous membrane and a fluorescence region, which includes the chemical fluorescence, in a feature space formed by the plurality of pieces of color information, by expanding a chroma saturation difference and a hue difference between the normal mucous membrane and the fluorescence region.

\* \* \* \* \*